(12) United States Patent
Lines et al.

(10) Patent No.: US 6,489,915 B1
(45) Date of Patent: Dec. 3, 2002

(54) MICROWAVE ICING AVOIDANCE SYSTEM

(75) Inventors: R. Todd Lines, Rochester, NY (US); Richard C. Savage, Franktown, CO (US); Jim Cole, Aurora, CO (US)

(73) Assignee: Raytheon Company, Lexington, MA (US)

( * ) Notice: Subject to any disclaimer, the term of this patent is extended or adjusted under 35 U.S.C. 154(b) by 64 days.

(21) Appl. No.: 09/710,141

(22) Filed: Nov. 9, 2000

Related U.S. Application Data

(60) Provisional application No. 60/165,233, filed on Nov. 11, 1999.

(51) Int. Cl.[7] .............................................. G01S 13/00
(52) U.S. Cl. ................................................... 342/26
(58) Field of Search ................................... 342/26, 460

(56) References Cited

U.S. PATENT DOCUMENTS

| | | | |
|---|---|---|---|
| 4,873,481 A | | 10/1989 | Nelson et al. ........... 324/58.5 R |
| 5,028,929 A | * | 7/1991 | Sand et al. .................... 342/26 |
| 5,488,375 A | * | 1/1996 | Michie .......................... 342/26 |
| 5,777,481 A | * | 7/1998 | Vivekanandan ............. 324/640 |
| 6,125,327 A | * | 9/2000 | Kalenian ........................ 702/3 |
| 6,184,816 B1 | * | 2/2002 | Zheng et al. .................. 342/26 |

FOREIGN PATENT DOCUMENTS

EP 0 667 518 A2 8/1995 .......... G01N/22/04

OTHER PUBLICATIONS

International Search Report dated Nov. 8, 2001 for PCT/US 00/31207 filed Nov. 13, 2000.

* cited by examiner

Primary Examiner—John B. Sotomayor
(74) Attorney, Agent, or Firm—Baker Botts L.L.P.

(57) ABSTRACT

A passive microwave icing avoidance system (MIAS) senses atmospheric conditions that lead to aircraft icing when the aircraft is flying at an altitude above the earth's surface. The MIAS includes a 37 GHz receiver and an 89 GHz receiver coupled to an antenna for sensing two microwave frequencies at different angles creating six passive microwave beams. The two receivers output data to a processor that processes the data to determine the amount of cloud liquid water and generates signals to an indicator/display to instruct the pilot of an aircraft to divert or proceed along the flight path.

37 Claims, 9 Drawing Sheets

MICROWAVE ICING AVOIDANCE SYSTEM

RELATED APPLICATION

This application claims the benefit of U.S. provisional application Ser. No. 60/165,233, filed Nov. 11, 1999, entitled Microwave Icing Avoidance System.

TECHNICAL FIELD OF THE INVENTION

The present invention relates to a passive system and method for measuring the amount of liquid water in the atmosphere and the temperature of the water for a determination whether ice will form on the airframe, and more specifically to a microwave icing avoidance system and method using a passive radiometer utilizing either a single frequency or two frequencies of passive remote sensing microwave energy for monitoring the severity and type of ice in a cloud formation.

BACKGROUND OF THE INVENTION

Aircraft icing is caused by flight into areas of supercooled cloud water or drizzle, that is, water remaining liquid at temperatures below 0 degrees Celsius (273 K). This is a rather common situation in Fall and Winter, especially at altitudes flown by commuter aircraft and aircraft in holding patterns for an airport. There is no known existing operational passive system or method for recognizing the conditions of supercooled liquid water and/or drizzle in clouds that cause aircraft icing.

U.S. Pat. No. 5,028,929, "Icing Hazard Detection for Aircraft" describes a dual-frequency radar system for recognizing the presence of liquid and drizzle droplets in a cloud. However, the radar, which measures energy backscattered from the droplets, cannot estimate droplet temperature. Accordingly, the system described in this U.S. patent cannot tell if water droplets are supercooled (i.e., at a temperature below 273 K) and about to freeze, or whether they are above 273 K and cannot freeze. In addition, the radar system cannot distinguish between liquid water drops, which can cause icing and frozen ice pellets, which are not known to contribute to aircraft icing.

Passive microwave sensors have been used in meteorological satellite programs such as the Defense Meteorological Satellite Program (DMSP) and the Tropical Rainfall Measurement Mission (TRMM) for several years for the study of cloud water content and temperature (Jansen, Michael A., 1993: Atmospheric Remote Sensing by Microwave Radiometry, Wiley Series in Remote Sensing, and Stephens, G. L., 1994: Remote Sensing of the Lower Atmosphere, Oxford Univ. Press). The need for the remote detection of aircraft icing conditions, and the DoD need for covert capability lead to considering this technology for aircraft.

SUMMARY OF THE INVENTION

In accordance with the present invention, there is provided a microwave icing avoidance system utilizing a passive microwave radiometer operating at frequencies above and below the 50–60 GHz oxygen absorption band, and observing for cloud droplets or drizzle droplets in the atmosphere ahead of an aircraft or upwind from an airport at three angles of observation: horizontally, and at + and −2° from the horizontal.

The microwave icing avoidance system (MIA) system of the present invention provides information to a pilot of potential icing conditions ahead of the aircraft (at a distance up to 50 km) or approaching an airport in time for rerouting above, below, or around the danger area. The MIA system also provides the ability to recognize external areas of lesser icing potential from inside an area of icing occurrence. Thus, a pilot who inadvertently enters icing conditions may be able to chart a path out of the area of possible icing conditions.

The use of a passive system is fundamental to the physics of the aircraft icing problem. In addition to detecting the presence of liquid water in the form of cloud droplets or drizzle droplets, an icing avoidance sensor determines whether the cloud droplets are supercooled (that is, at a temperature less than 273 K) or not. Supercooled cloud or drizzle droplets are liable to freeze upon the surface of an aircraft. Droplets above 273 K, on the other hand, usually do not form ice upon the surfaces of an aircraft. A passive icing avoidance system detects the droplets by measurement of emitted radiative energy; such emitted energy is uniquely characteristic of the temperature of the emitter at a given microwave frequency (as given by Planck's Law).

In addition to being suited to measuring the temperature of liquid droplets in the atmosphere, passive microwave measurement systems are capable of recognizing the difference between liquid droplets and frozen species. This is because the dielectric constant of ice is small, leading to low emissivity by ice. This means that the dangerous supercooled liquid droplets emit most of the radiance sensed by the MIA system radiometer. Since frozen droplets usually do not cause further icing to the surfaces of an aircraft, recognition of the presence of frozen droplets allows the pilot to go safely into the area where such droplets occur. Radar devices, working on the principle of scattering, cannot make this distinction, since ice particles do scatter the radar energy.

The Radiative Transfer Equation (RTE) enables the determination of the brightness temperature coming to the sensor. The brightness temperature depends on the integrated product of the temperature and the derivative of transmissivity along the viewing path. This enables the recognition of the presence of cloud droplets and drizzle droplets by the change caused in transmissivity so long as the viewing path is not horizontal, since the atmosphere tends to be isothermal along a horizontal path. to Accordingly, MIA of the present invention utilizes slightly slanted paths above and below the flight path.

The Mie theory has been utilized in the development of the MIA system of the present invention. According to the Mie theory, the absorption and emission characteristics of a liquid water droplet increases rapidly as the ratio of droplet circumference to wavelength approaches unity. This physical law allows the MIA system to distinguish between ordinary cloud droplets (which are typically about 10 millionths of a meter in diameter) and drizzle droplets (which are typically 350 millionths of a meter in diameter). The MIA system makes use of two different frequencies, such as 37 GHz and 89 GHz, having wavelengths of 8.1 and 3.3 mm respectively. Ordinary cloud droplets have little absorption at both frequencies, since the droplet circumference is small in comparison to the wavelength. However, drizzle droplets have a large absorption and emission at 89 GHz, since the ratio is almost unity.

The MIA system of the present invention utilizes two frequencies to take advantage of Mie theory to "see" the droplets in different ways and estimate the water content from the comparison. In addition, the MIA system enables a determination of the distinction between ordinary cloud droplets (usually causing only rime icing) and drizzle droplets, which cause clear icing that may spread beyond the deicing equipment of an aircraft. The tendency of clear ice to freeze slowly and spread beyond ice removal equipment makes this class of ice much more dangerous than rime ice.

Because the MIA system of the present invention is based on the fundamental principle of recognizing the transmissivity decrease caused by liquid water droplets, such a system has additional application. Since droplets reduce transmissivity, rain of intensity greater than drizzle is also very visible in the MIA system, and solid objects such as mountain tops or buildings will also be rendered visible to the pilot within a veil of cloud droplets or haze. Thus the MIA system provides additional flight safety functions related to other weather phenomena and terrain avoidance.

It is also known that a water surface (as distinct from water droplets suspended in air) look much different from land surfaces, whether vegetated, snow covered, or bare soil. The MIA system data, if presented as an image, has utility as a passive, all-weather imager, showing coastlines, water bodies, glaciers, and other natural features, for purposes of navigation. To some extent the MIA system of the present invention performs many functions of a radar, without the cost, power, and overtness of radar transmissions.

The MIA system, in one embodiment, utilizes only one frequency (37 GHz), with a single polarization, and provides information (temperature, liquid water content) sufficient to warn a pilot of icing conditions ahead. For the pilots not qualified to fly into icing conditions, this is all the information needed; they must reroute to avoid the icing conditions. For the smaller but more professional cadre of commercial pilots who are qualified (with appropriate aircraft deicing equipment) to enter icing conditions, an alternate embodiment of the MIA system uses dual frequencies (37 GHz and 89 GHz) and dual polarization at the higher frequency, provides information to enable the distinction between rime ice (which can be removed in flight by deicing boots) and the deadly clear ice. Most commercial flights (and military flights) could proceed with the knowledge that only rime ice is to be expected. This permits optimization of flight operations, rather than unqualified termination for any icing conditions.

BRIEF DESCRIPTION OF THE DRAWINGS

A more complete understanding of the microwave icing avoidance system of the present invention may be had by reference to the following detailed description when taken in conjunction with the accompanying drawings.

DETAILED DESCRIPTION OF THE INVENTION

Figure 1:
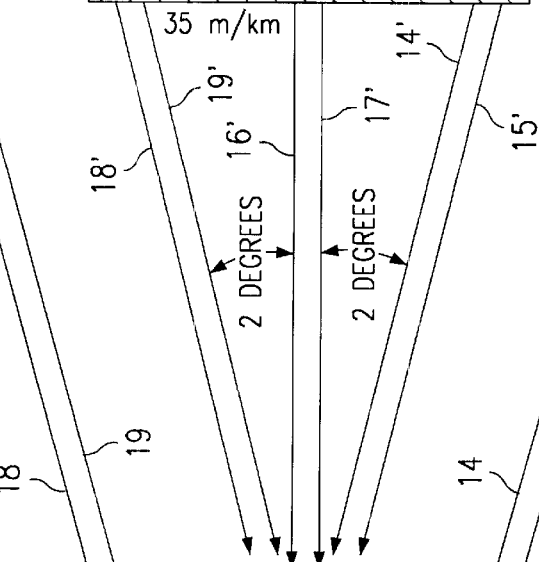
FIG. 1 is an illustration of an aircraft equipped with the microwave icing avoidance system of the present invention approaching a cloud containing conditions for possible icing.
Figure 1:
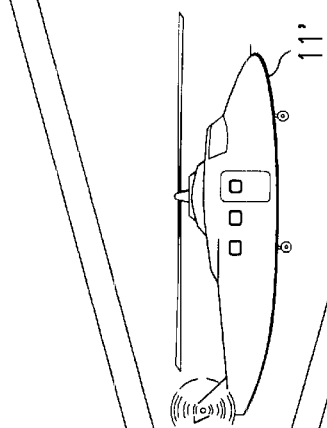
Figure 1:
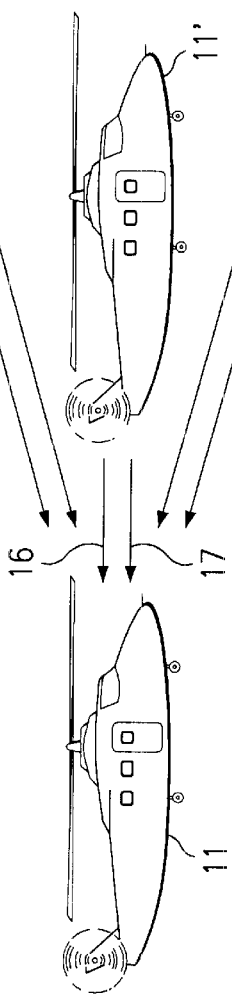

Referring to FIG. 1, there is shown an aircraft 11 equipped with a passive microwave icing avoidance system (MIAS) for sensing the atmospheric conditions that lead to aircraft icing ahead of the aircraft flying at an altitude above the earth's surface. Located in the flight path of the aircraft 11 is a cloud containing icing conditions 12. Two microwave frequencies are detected at different angles along six passive microwave beams 14, 15, 16, 17, 18, and 19. One frequency is located in the 36–37 GHz band, a frequency band that is reserved for remote sensing use. The second frequency is located in the 86–92 GHz band, also reserved for remote sensing use. The higher frequency (86–92 GHz) is dual polarized (vertical and horizontal). These beams are received from the cloud hydrometeors causing the icing conditions 12, and are received by a radiometer as a part of the MIA system to be described.

When the aircraft 11 is at a considerable distance from the icing conditions, the upward beams 18, 19 represent emission of the low radiometric power from space and the upper atmosphere. The downward beams 14, 15 represent emission of the warm surface of the earth. The forward looking beams 16, 17 represent emission of the atmospheric conditions ahead of the aircraft 11. As the aircraft 11 (aircraft 11') approaches the icing conditions 12 the upward beams 18', 19' respond with a strong rise in signal strength; likewise, the downward beams 14', 15' respond with a quick diminishing of signal strength as these beams intersect the icing conditions 12. The received power from each of the six beams 14', 15', 16', 17', 18', and 19' is compared to previous power levels in the corresponding beam 14, 15, 16, 17, 18, and 19 by processing in the MIA system to be described. The processing by the MIA system determines the amount of liquid water in a cloud and the temperature of that water. Depending upon the ability of the aircraft 11 to de-ice, the pilot receives information to divert or to proceed along the flight path. Information from only the lower frequency is adequate to warn a pilot of an aircraft that does not have equipment to de-ice in flight; a simpler version of the MIA system is adequate for this case.

Passive microwave sensors, operating at wavelengths of a few millimeters (between 30 and 100 GHz) are capable of sensing conditions—temperature, water content—for long distances (25–50 km) ahead of the aircraft, operating in and through clouds. At the same time, these sensors provide signals to estimate the temperature of the liquid water in the atmosphere ahead of the sensor, similar to IR sensors.

In accordance with the present invention, the MIA system provides remote detection of the presence of liquid water in the atmosphere at near flight level of an aircraft. "Remote" is determined by aircraft speed, since 5 or 6 minutes is required for ATC approval of a course change. For speeds between 120 and 250 km/hr, this implies remote detection at greater than 25 km, and greater distances if possible. At a distance of 25 km, the 2° upward looking beam 18, 19 of FIG. 1 is 875 m above flight level, that is, beams 16, 17.

Since supercooled liquid water leads to icing, both the temperature and water phase of the water are important. Liquid water warmer than 273 K is unlikely to cause icing. Likewise, pellets of ice, sleet, or other frozen hydrometeors are not an icing hazard per se.

The icing hazard to an aircraft is dependent upon liquid water content, droplet size distribution, temperature, and airframe configuration. In addition, it is also useful to provide an estimate of the liquid water content of the clouds ahead.

Explicit identification of large drizzle drops, a source of very hazardous clear icing, is an output of the MIA system. Ordinary cloud droplets are less dangerous for icing.

A passive microwave system, unlike radars (active microwave systems), cannot separate the received signal into parts on the basis of time (and therefore distance). The energy received (described as a brightness temperature, $T_B$) comes from the integral of thermal energy along a path, as indicated in Equation 1:

$$T_B(f) = \int_0^\infty T(s') \exp[-\int_0^{s'} k(f,s)ds] k(f,s') ds' \; 0 \leq s' \leq s_{max} \quad (1)$$

where f is the operating frequency, s' is the path variable (extending from 0 at the sensor to a maximum sensing distance $s_{max}$), T(s') is the thermometric temperature along the path, and k(f,s) is the attenuation coefficient—a function of both frequency and the distribution of attenuating phenomena along the path. Brightness temperature, $T_B$, is a convenient alias for radiometric energy in the microwave spectrum, where radiant energy is linear with temperature. This form of the equation for brightness temperature explicitly identifies the elements of transmissivity $\tau = \exp(-k*s)$. The elements inside the integral sign of equation 1 are simply $d\tau$, and the integral over $d\tau=1$. From Equation 1 it will be noted that if the thermometric temperature T(s') is constant along the path, it could be removed from the integral sign. Viewing horizontally is a good way to measure temperature ahead on the flight path, but not a good way to recognize changes of liquid water content.

The integrated effect is analogous to sound, reaching us from many points along a path to our ear. A strong sound signal (say, a marching band in the distance) may be "drowned out" by a nearby person whispering to us. A passive microwave signal from a supercooled cloud in the distance could be "drowned out" by oxygen and vapor closer to the aircraft. It is an objective to minimize such effects, though such effects cannot be completely overcome.

Referring again to FIG. 1, in the analysis considered here, k identifies molecular oxygen, water vapor, cloud liquid water, and (sometimes) drizzle drops. When displaying the sensor response for observation, the relative or absolute magnitude of these constituents is difficult to observe—that is, the sensor output is the result of integration along the beam path. Using the above sound analogy, it is difficult to tell "how loud the band is playing" when someone is whispering to us. Therefore, when there is maximum attenuation close to the sensor, most of the sensor signal will represent that part of the path; when the maximum attenuation is at a distance, most of the signal will come from the distant location. The MIA system makes cloud and drizzle signals available for observation a sufficient distance ahead of an aircraft, and to minimize the sensor signal from atmospheric elements (oxygen, vapor) that contribute little to the icing phenomenon. The MIA system maximizes the signal from the dangerous elements—the clouds and drizzle—and minimizes signals from clear air.

Figure 2:
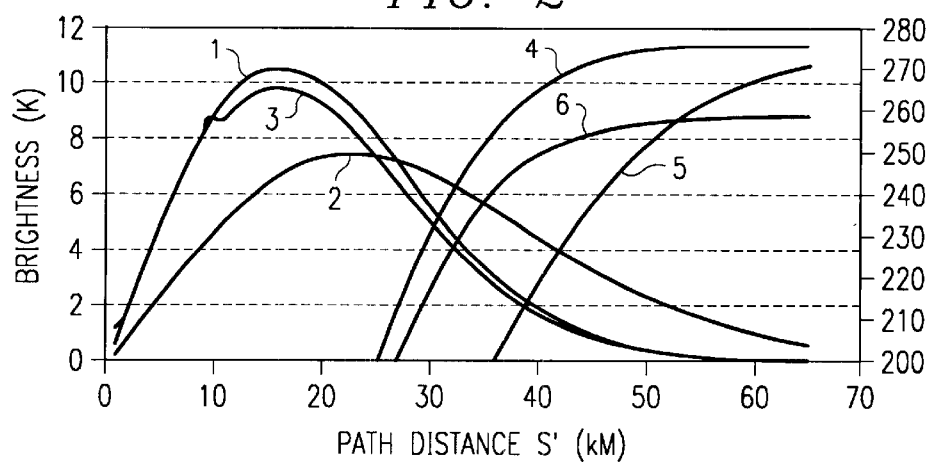
FIG. 2 is a plot of brightness as a function of path distance knowing the variables of integration as temperature changes.

Referring to FIG. 2, there are six curves, plotting the values inside the integral sign of Equation 1 and related integrated values. The integrated values (rising monotonically to the right) are plotted on the right axis; the curves which first rise, then fall, represent the values being integrated. The integrated values represent sensor response; the peaked curves show the response along the flight path (the granularity is 1 km.).

The first curve 1 is a plot of the variable when the thermometric temperature T(s') is constant and the attenuation k(s') equals 0.002/km. (T(s') equals 275.16 K, the temperature at 2.0 km flight level in the U.S. Standard Atmosphere.) As can be seen, the maximum contribution (the peak of the curve) comes from about 15 km in front of the sensor, with limited contributions from closer and from farther away, decreasing to nearly zero at about 60 km. If attenuation along the path decreases to 0.001 /km, then the second curve 2 represents the variables. It should be noted that the maximum contribution (the peak) is farther from the origin (there is less attenuation between the origin and 15 km than before), and the signal is integrated over a greater distance (to about 70 km). This illustrates that increased attenuation (k (s')) brings the peak of the response closer to the sensor. Increased attenuation would result from liquid water in a cloud along the beam path, such as shown in FIG. 1. If no cloud is present, the sensor responds to farther atmospheric events. Since the temperature is assumed constant along the beam path, the integrated value under either curve (curves 4 and 5 plotted on the right axis) is 275.16 K. Naturally, the lower attenuation curve takes longer to integrate to 275.16 K.

If the temperature decreases along the path to 255.16 K at the 11 km point (curve 3), the integrated value (curve 6) is seen to level off at about 259 K (less energy is received from the colder air). This illustrates the ability to measure an integrated temperature along the path in front of the aircraft 11—useful information when looking for supercooled water ahead, not just at the cockpit. When observing changing temperatures ahead of the aircraft 11, the brightness signals from the sensor are composed of an integration over the path. A small effect is observable when the change is far ahead, but the response from the sensor will increase as the aircraft approaches the cloud 12. The plots in FIG. 2 are valid for an instantaneous path; there will be described plots of brightness as an aircraft flies through the atmosphere.

However, the plots of FIG. 2 illustrate that an attenuation change along the path cannot be measured if the temperature is constant. Curves 1 and 2 integrate to the same value (275.16 K), shown in curves 4 and 5, in spite of the different attenuations. As noted above, this is because integration over transmissivity, over $d\tau$, equals 1. Looking along a horizontal path, when the temperature is constant along the path, it is difficult to tell the difference between clear and cloudy air, nor make any estimate of the amount of liquid water in a cloud (which affects the attenuation). However, the maximum response—the peak of the response—moves closer to the sensor if attenuation increases, and moves farther away for decreasing values of attenuation. The MIA system utilizes changes of attenuation—due to liquid water in clouds—along a path in front of the aircraft 11.

Figure 3:
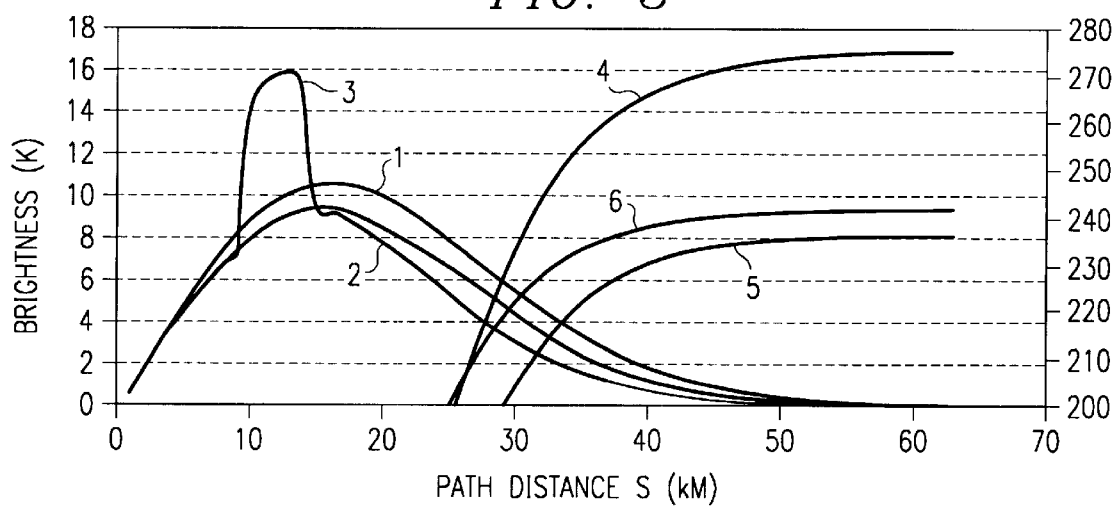
FIG. 3 is an illustration of six more curves similar to FIG. 2 showing brightness plotted as a function of distance with variable temperature and attenuation along a flight path.

Referring to FIG. 3, there is illustrated six more curves, curves 1 and 4 are as before—constant temperature along the path and constant attenuation. Curve 4 represents the output of the sensor, integrated over the path, and is equal to 275.16 K. In curve 2, the temperature decreases by a fixed amount (2 K) per kilometer along the flight path. Naturally, curve 5 shows a lesser integrated output from the sensor— about 236 K. The effect is similar to the comparison between curves 1 and 2 (and curves 4 and 5) in FIG. 2. Lower thermometric temperature T(s') along the path produces a lower 25 brightness signal—less energy—out of the sensor.

Now, considering curve 3 (and the corresponding integral, curve 6), when the attenuation coefficient k(s') is increased between 10 and 15 km: (temperature decreases along the path, as in curve 2). The change in the height of the peak is as expected, but the location of the peak has moved closer to the sensor, as shown in FIG. 2 when attenuation increased. Since temperature decreases along the path, movement of the peak response closer to the sensor—as a result of increased attenuation—also increases the brightness signal output from the sensor, as observable from the integrated value of curve 6, about 241 K. If temperature increased along the path, the increased attenuation would decrease the output of the sensor. Note also there is less response from curve 3 than curve 2 beyond 15 km; as in FIG. 1, there is less response from beyond the cloud. It is known that temperature usually increases along a downward path, and decreases along an upward path (in the troposphere, where icing is a hazard). Of course, liquid water in clouds results in increased attenuation along the path; clearing decreases attenuation.

Though this description has referred to k(s') as the attenuation coefficient, there is also some effect on the amount of energy emitted by different parts of the atmosphere. This is a manifestation of Kirchoff s Law of Thermal Radiation ("a good absorber is a good emitter"). Variations of attenuation along the path of the sensor will have an effect on the signal received if there is a temperature change along the path. Curves 3 and 6 in FIG. 3 illustrate how this is used to an advantage.

To observe icing conditions, a signal is needed that varies when a cloud (an attenuation change) lies ahead. Such a signal can be obtained if the angle of the integration path (beams 18, 19) is upward, allowing the temperature to decrease along the path (as it usually does in the atmosphere). If there is little attenuation along the path, the sensor output will represent an integral of radiant energy from farther colder points on the path. If there is liquid water and increased attenuation in part of the path (as shown in FIG. 2), the increased response from a warmer part of the path will increase the output brightness. This has the additional advantage that more liquid water content in the atmosphere will increase the brightness to a greater extent than a small liquid water content.

For the conditions previously described, only instantaneous response to a finite cloud have been shown, for example, the cloud in FIG. 3 is only 5 km thick, and there is some response from beyond the cloud. However, a thick cloud 25 km or so thick, with no radiation coming from beyond the cloud, will show the effect of sensor movement, as the sensor approaches the cloud. The brightness output from the sensor will increase as long as the integrated water content along the path is increasing. At some point the sensor output will level off or begin to decrease, as the other side of the cloud comes into view—as attenuation decreases.

Since the MIA system is measuring integrated air temperature (straight ahead) and water content (upward or downward) on different paths ahead, there is a potential adverse effect. At 25 km ahead, the end points of the paths are 875 m apart with a 2° angle. There is some potential here for a "false alarm" due to cloud water entirely above the flight level that may not actually be flown through. This is, at least, better than not seeing a cloud that is a potential threat.

The identification of the presence of a cloud cannot be made until it impinges into the upward or downward beam 18, 19, so it must extend above or below the flight level for the aircraft 11 at least 875 m to be visible 25 km ahead. A lower cloud (relative to flight level) remains "hidden" longer.

FIGS. 2 and 3 illustrate the result of radiative transfer. A change of thermometric temperature along the path of integration (the path the sensor is seeing) will be observable by a change in the output of brightness temperature from the sensor (compare curves 1 and 2 in FIG. 3). Likewise, changes of attenuation (and, therefore, of emissivity) change the point along the path from which the sensor receives the most signal. If thermometric temperature along the path is warmer close in, and colder farther away, a cloud—more attenuating than clear air—will provide more signal from the warmer part of the path, and block some of the energy from the cold part of the path. Therefore, it is necessary to be able to calculate the amount of attenuation from real atmospheric constituents—oxygen, water vapor, clouds—along a path with horizontal and vertical variations of these constituents.

Both oxygen and water vapor emit energy in well-known frequency bands in the microwave spectrum. As noted in Equation 1, the attenuation, k, is a function of frequency. Careful choice of frequencies where emission from oxygen and vapor does not obscure the cloud or drizzle emission must be made. The bands of frequencies where the atmosphere becomes opaque due to these gasses are shown in FIG. 4.

Figure 4:
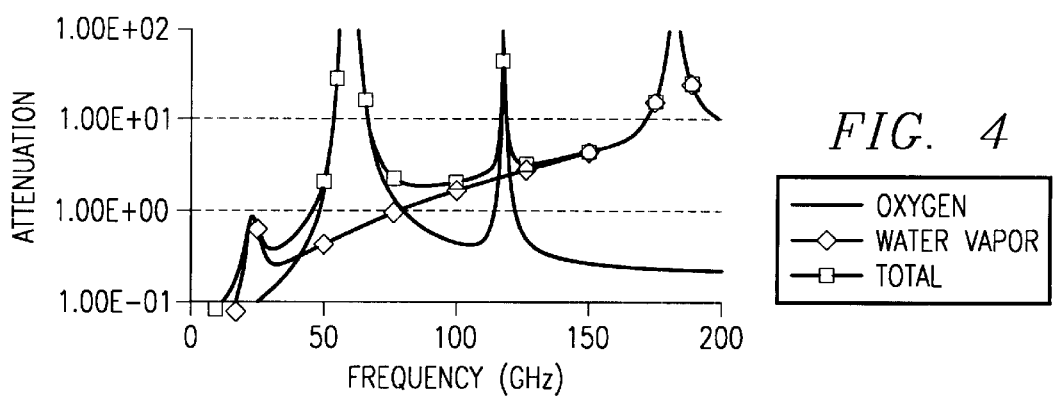
FIG. 4 is a plot of atmospheric attenuation by oxygen and water vapor in a clear atmosphere.

Relatively clear portions of the spectrum ("windows"), as shown in FIG. 4, are between 30–50 GHz, between 70–110 GHz, and beyond 120 GHz up to 150 GHz. It is important to avoid frequencies where transmitters would interfere. The bands 36.0–37.0 and 86.0 to 92.0 GHz have been designated as "quiet bands", reserved by government regulation for remote sensing. Both these bands have been used in previous and current satellite microwave sensors for estimation of cloud water content. As illustrated in FIG. 4, these frequencies are in "windows" of the microwave spectrum. Hereafter, reference will be made to these two bands as "37 GHz" and "89 GHz."

Referring to FIG. 4, the strong attenuation band from 50 to 60 GHz is used by satellite sensors for estimation of temperature profiles. Frequencies up to 52 GHz are not protected against transmitter interference; above 52 GHz, there is so much attenuation by clear air it would be difficult for the MIA system to recognize icing conditions at the desired distance of 25 km or more.

Since the cloud droplets and drizzle of interest are liquid water, with a known dielectric constant, their radiative characteristics are governed by the laws formulated by G. Mie and begun by Lord Rayleigh (Stephens, 1994). These laws define how the absorption by water droplets depends on their size ratio—the ratio of droplet circumference ($2*\pi*r$) to wavelength ($\lambda$). The absorption increases (very nonlinearly) with increasing size ratio, reaching a maximum when the size ratio equals 1.0. In nature, cloud droplets range from a micrometer in radius up to 25 or more micrometers. Drizzle-sized drops are several hundred micrometers in radius. This means cloud droplets have small but different size ratios at 37 GHz and 89 GHz, and absorb more at 89 GHz than at 37 GHz. The drizzle-sized drops also appear much larger at 89 GHz than at 37 GHz, and absorb much more. Different sensor frequencies are used to provide different k (s') values when observing clouds.

The difference of absorption due to a difference of size ratio allows obtaining information by observing the droplets at different wavelengths. Since temperature decreases with height in the troposphere, looking upward normally results in a colder brightness temperature than looking ahead. An upward-looking beam at 37 GHz sees farther through a cloud than the 89 GHz beam, resulting in a colder brightness temperature than at 89 GHz. This difference of brightness leads to an estimate of liquid water content. The greater the difference of brightness, the less water is present; large water content causes the brightness temperatures to be close together—only a few degrees, or even zero.

Using different frequencies (37GHz and 89 GHz) to avoid attenuation by clear air (oxygen and vapor), which do not contribute to aircraft icing, obtains different attenuation characteristics from clouds and drizzle droplets. By taking advantage of international agreements to exclude transmission in these bands, there is the potential for passive observation without interference.

Attenuation is comprised of two processes, absorption and scattering. Scattering—as the word implies, is a redistribution of energy—becomes important when the size ratio—the ratio of drop circumference to wavelength, ($2*\pi*r/\lambda$)—becomes larger than 0.1. Since a cloud droplet 10 micrometers (0.01 mm) in radius has a size ratio less than 0.02 at 89 GHz ($\lambda=3.4$ mm), scattering has not been thus far considered.

In addition to emissivity differences, drizzle drops (but not ordinary cloud droplets) will exhibit scattering of radiant energy at 89 GHz—a redistribution of energy into many directions, like sunlight seen inside a cloud. At 89 GHz, a 400 micrometer radius (0.4 mm) drizzle drop has a size ratio of 0.75 and scattering will be significant.

Scattering is considered a loss mechanism—part of the attenuation process—because it removes energy from the original path of propagation. However, scattering can also be considered a generation mechanism for a sensor if scattering causes energy to be diverted into the direction of the sensor where none was propagated before. This, of course, is how cloud precipitation radar works—energy is scattered back to an observer from droplets. Clear air cannot scatter, so there is a contrast between rain and clear air or clouds. To make use of this scattering property, it is necessary to recognize a signal that warns that drizzle is present. Freezing drizzle is hazardous to all aircraft—even those with deicing equipment—since it leads to clear ice.

Figure 5:
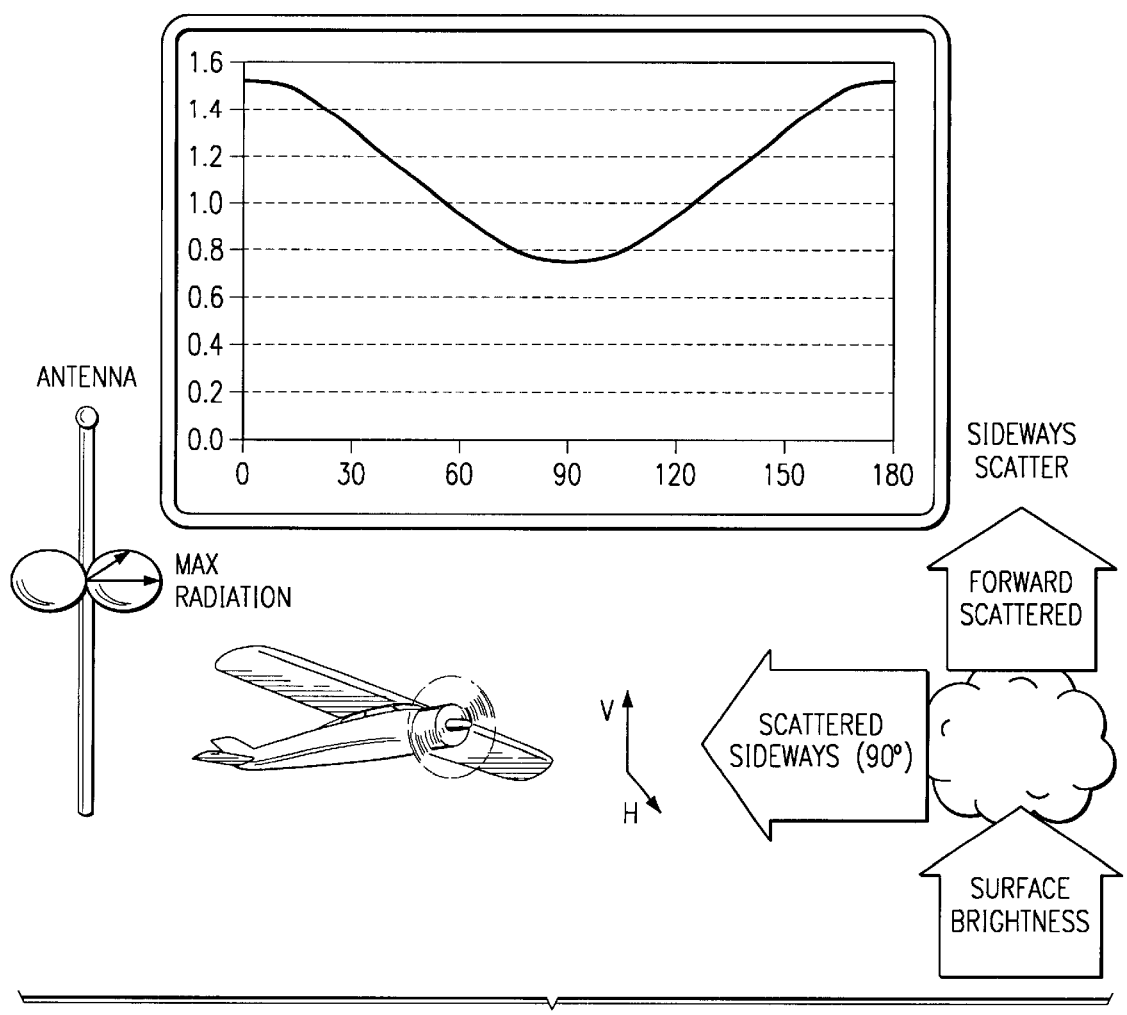
FIG. 5 is an illustration of scattering of surface brightness introducing additional definitions regarding the scattering and polarization for an understanding of the microwave icing avoidance system in accordance with the present invention.

To proceed with a description of the invention, additional definitions will be introduced in regard to scattering and polarization. Referring to FIG. 5, polarization is measured by the response of an isolated positive point charge by a passing electric field. If the point charge moves only in a vertical plane, the field is vertically polarized; if the point charge moves only in a horizontal plane, the field is horizontally polarized. For an airborne sensor, the vertical plane is the plane of the vertical stabilizer; the horizontal plane is the plane of the wings and horizontal stabilizer. Energy that is emitted directly from the atmosphere—from oxygen, vapor, cloud droplets, or drizzle drops—is unpolarized— that is, there is equal energy in either measurement plane.

Scattering is the result of drizzle drops acting like small antennas. Like dipole antennas, drizzle drops radiate best in the plane perpendicular to the antenna orientation, as shown at the top left of FIG. 5. Drizzle drops scatter poorly in the plane of the wings —the horizontal plane. Scattering, if present, can therefore be observed by measuring the degree of polarization. Atmospheric emission is unpolarized, so observation of a polarized signal is a sign that large drops are present, causing scattering to occur.

Polarization is the result of two processes:
1) Microwave energy emitted from water or moist land surfaces is already polarized; that is, the apparent temperature in the vertical plane of polarization is greater than that in the horizontal. Since the upward flux over water or moist land is already polarized, energy scattered to the upward or straight ahead beams of a sensor by drizzle drops will also be polarized. This is an indication that drizzle is present, since emission from cloud droplets and atmospheric gasses (oxygen, vapor) is not polarized. The downward beam of a sensor has the possibility of seeing the surface and its polarized emission directly, so is a less reliable clue of drizzle.
2) Heavy vegetation and dry land are unpolarized, that is, the brightness temperature is the same in either plane of polarization. However, because the drops scatter less energy into the plane of the aircraft, a polarization is introduced by the scattering—which occurs only when relatively large drizzle drops are present. Accordingly, energy emitted from the cloud and surface, then scattered into the forward-looking beams of the MIAS radiometer will look (slightly) warmer in the —vertical plane of polarization than in the horizontal. This is another indication that drizzle-drops and potential clear icing are present. However, the amount of polarization at the sensor will be less in this case than when the upwelling brightness is already polarized.

As previously described, the emissivity of a particle depends on its dielectric constant. In accordance with the laws of physics, the dielectric constant of ice is very different from that of water. Ice has very low emissivity, making it almost invisible, regardless of its real temperature. This is fortunate because the MIAS sensor is looking for the liquid species having properties that cause freezing on an aircraft, and the already-frozen species, which is not a danger, is almost invisible and thus not a distraction.

Unfortunately, ice particles are capable of scattering. However, as in the case of liquid drops and droplets, relative size between cloud particle and wavelength is important. Frozen cloud droplets—relatively small at the wavelengths of interest—are not considered to cause enough scattering to give a "false alarm" indicating drizzle ahead. Frozen drizzle could cause enough scattering to give a "drizzle ahead" signal. The clear icing that would result from liquid droplets of equal size would not occur, since these particles are already frozen. The MIAS may give a "false alarm" in this case, a condition that is at least better than failure to indicate a true danger.

Figure 6:
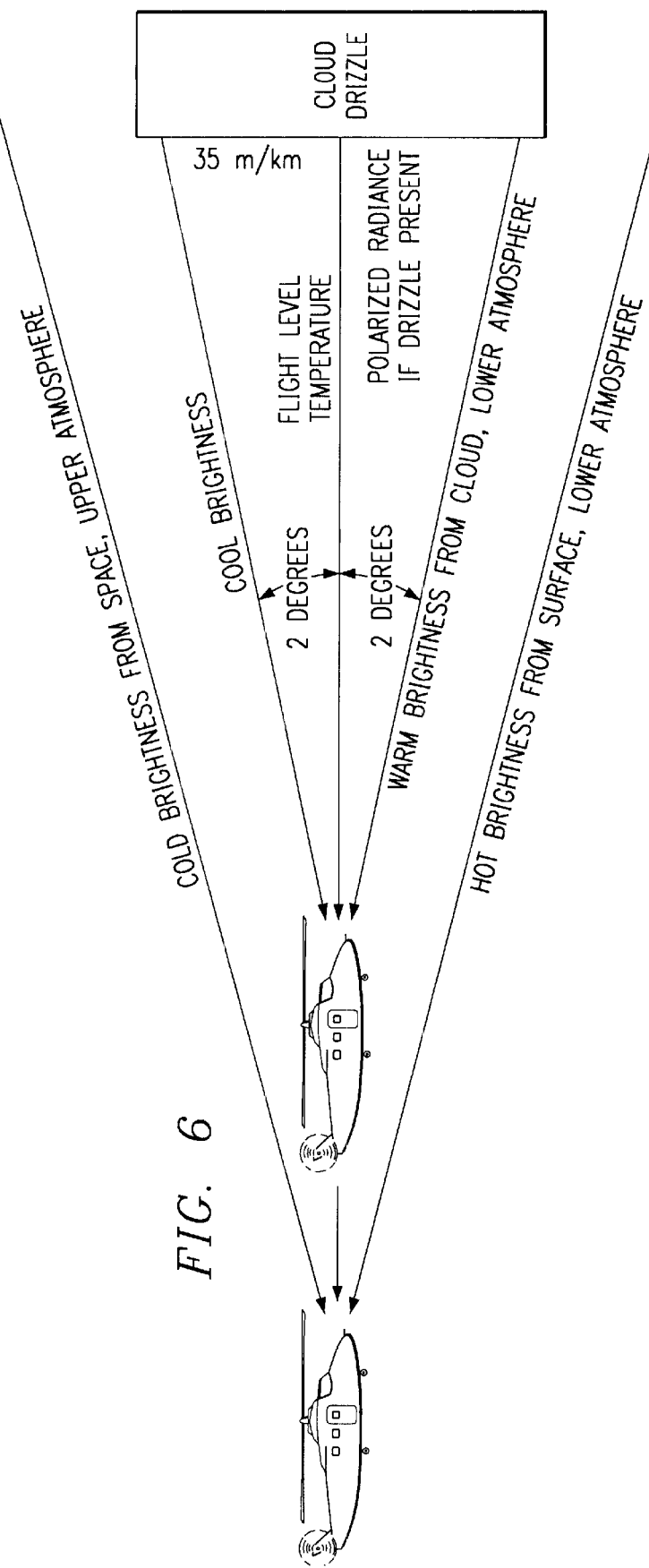
FIG. 6 is an illustration of an aircraft equipped with a microwave icing avoidance system of the present invention approaching a symbolized cloud showing different sensing angles to locate the cloud ahead.

Based on the preceding description, it is possible to formulate a MIAS radiometer having principal features are shown in FIG. 6.

Two frequencies, 37 GHz and 89 GHz, are utilized and three sensing beams, arranged in a vertical pattern of +2°, 0° (i.e., ahead at flight level), and −2°. The 2° beams rise and fall 35 meters per kilometer, respectively. From a distance of 25 kilometers, with a lapse rate near 6 K /km, either beam should "see" a part of the cloud that is (at least) 5 K warmer or colder than the flight level temperature, seen by the horizontal beam (provided the cloud extends to these altitudes). If, however, the cloud is not yet in view, the up and down beams will see much warmer levels below and much cooler levels above the cloud. Convergence of the measured brightness from the up and down beams toward the brightness of the horizontal beam is the first signal of approach toward a cloud (or drizzle, or rain). Distance can be estimated from the brightness difference between beams.

It is also important to estimate, while an aircraft is still at a distance, whether the cloud contains supercooled water. Since the MIAS radiometer measures brightness temperatures emitted from the cloud droplets, information about cloud water temperature is present. Either the 89 GHz or 37 GHz beam can be used for this purpose. Since the 37 GHz beam sees farther ahead than the 89 GHz beam, comparison of the brightness of the two beams indicates whether temperature ahead is increasing (37 GHz brightness>89 GHz brightness) or decreasing (37 GHz brightness<89 GHz brightness), as well as the absolute temperature (and whether water ahead is supercooled).

The third piece of information desired from the MIAS radiometer is an estimate of liquid water content, leading to an assessment of the severity and type of icing. Because the upward sensing beam penetrates farther at 37 GHz than at 89 GHz, the 37 GHz beam will measure a colder brightness temperature, probably containing emission from the upper troposphere and stratosphere. The 89 GHz brightness in the upper beam will be closer to the brightness in the straight-ahead beam. The closer together the 37 GHz and 89 GHz brightness temperatures in the upper beam, the more liquid water there is along a path common to these beams.

Since polarization may result from scattering of radiances at 89 GHz, the MIAS radiometer incorporates vertical and horizontal brightness measurements in the 89 GHz radiometer. Scattering is not expected at 37 GHz, so only a single polarization is needed.

Figure 7:
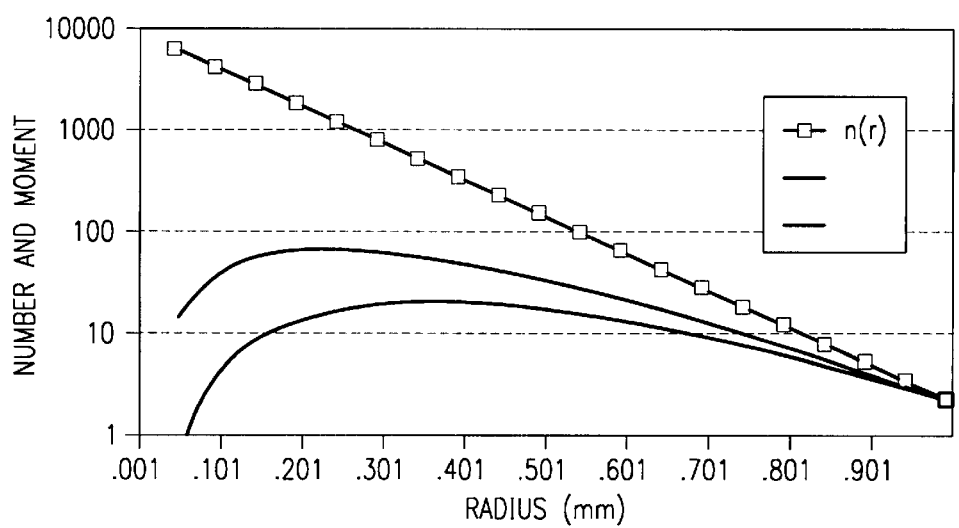
FIG. 7 is an illustration of a Marshall-Palmer drop size distribution (top curve), second moment (middle curve), and third moment (bottom curve) for a rain rate of 1 mm/hr.

Referring to FIG. 7, there is shown a chart of the drop size distribution (top curve), the second moment of the drop size distribution (middle curve), and the third moment of the distribution (bottom curve) f or a Marshall-Palmer distribution. The Marshall-Palmer distribution gives the number of raindrops per unit volume (in this case, per cubic meter) per unit radius per millimeter, in this case). The ratio of the third moment (the volume

TABLE 2

| Rate (mm/hr) | 0.5 | 0.75 | 1.0 | 1.5 | 2.0 |
|---|---|---|---|---|---|
| Water Content (g/m^3) | 0.049663 | 0.069816 | 0.0889 | 0.124974 | 0.159135 |
| Effective Radius (mm) | 0.313745 | 0.339593 | 0.35864 | 0.386283 | 0.406326 |
| Number (per cubic meter) | 408.0428 | 415.3493 | 422.5664 | 436.2523 | 448.8412 | of water in the drops) to the second moment (the surface area of the drops) gives the effective drop size—the radius of the average drop. For a rain rate of 1.0 mm/hr, the effective drop radius is 359 micrometers (0.359 mm). A tabulation for the drizzle rates from 0.5 to 2.0 mm/hr is given in Table 2. It may be seen that the effective size increases (from 0.314 mm to 0.406 mm) with increasing rain rate, and that the number of drops of the effective size increases as well (from 408 to 449 per cubic meter).

Figure 8:
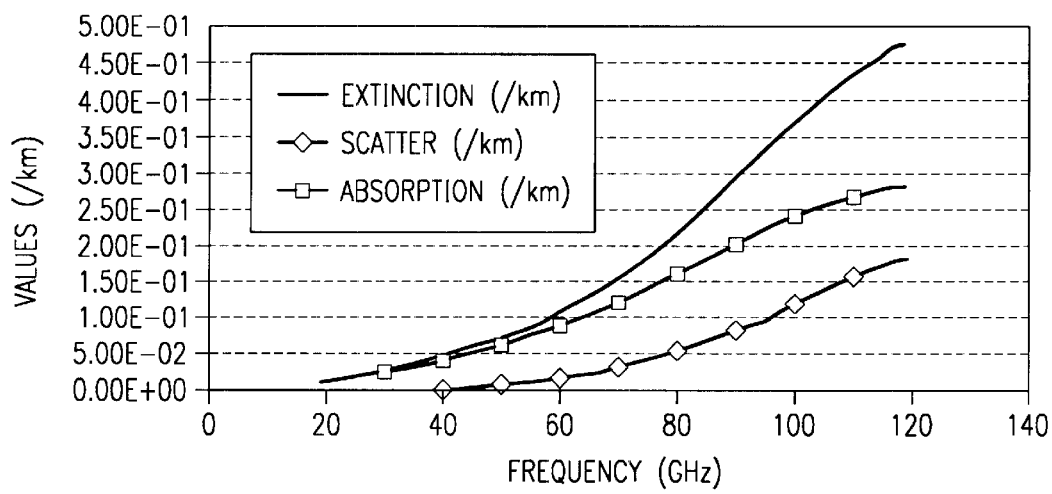
FIG. 8 is a plot of radiative characteristics (extinction, absorption, scatter) for a rain rate of 1 mm/hr.

Referring to FIG. 8, there is shown a plot of radiative characteristics (extinction, absorption, scatter) of an ensemble of effective droplet sized particles corresponding to 1.0 mm/hr, across a frequency spectrum from 19.35 GHz to 120 GHz. As previously discussed, scattering becomes more important at a higher frequency, such as 89 GHz, than at 37 GHz when drizzle is present. Scattering is unimportant at both frequencies for ordinary cloud droplets. Observation of the scattering effect will help remotely sense the presence of dangerous drizzle. This is dangerous even for aircraft with deicing equipment. It should be noted that the dimensions of the radiative characteristics are nepers/km. One neper/km equals 4.34 db/km (approximately). These calculations of radiative characteristics allows including drizzle attenuation along with the attenuation due to oxygen and vapor, see FIG. 4, and cloud droplets.

In FIG. 2 and FIG. 3, the horizontal axis is s', the path of integration from a stationary sensor. The integrated brightness (the sensor output) is also plotted as a function of path distance. In FIGS. 9 through 14, the aircraft is flying forward from a starting point at the origin, and the integrated output (the sensor reading) is shown for each successive measurement point.

Figure 9:
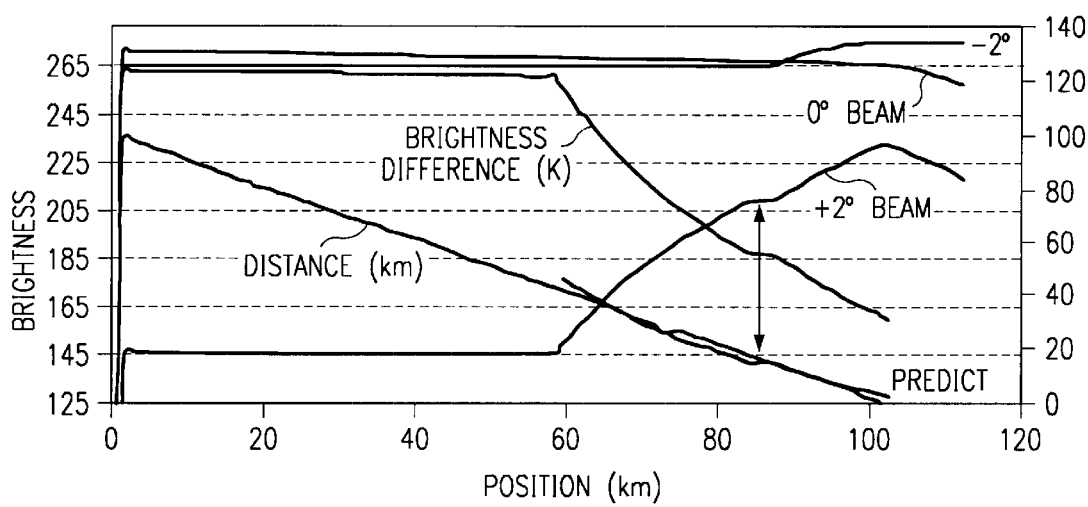
FIG. 9 is a plot of brightness reading from the sensor of the microwave icing avoidance system of the present invention as an aircraft approaches a cloud at 100 km from the origin.

FIG. 9 illustrates the brightness seen by the three 37 GHz beams, while flying toward a cloud whose forward edge is at 100 km from the origin. The cloud contains 0.1 gm/m^3 of cloud water in the levels from 2.0 to 4.0 km, and 1.0 mm/hr of drizzle between 2.0 and 3.0 km. Plotted on the horizontal axis is the position of the aircraft and sensor; the left vertical axis is the brightness temperature seen in the three sensing beams (+2, 0, and −2 degrees relative to horizontal). Plotted on the right axis is the brightness difference between the +2 and 0 degree beams, along with a predicted distance to the cloud, based on a linear regression fit to the brightness difference.

At the point where the upward beam encounters the upper front corner of the cloud (about 60 km from the origin), the brightness temperature begins a strong rise, continuing until the sensor enters the cloud (at 100 km from origin). This rise begins more than 40 km ahead of the cloud, and covers more than 80 K. The rise is due to the increase of emission from liquid water in the cloud. The peak response is closer to the sensor, and the emitted energy is from the troposphere, rather than the stratosphere and space. Since the noise level of the sensor is expected to be less than 0.2 degree K, this signal of cloud water ahead is quite definite. A cloud with a higher top (or higher relative to flight level) would be detected farther away. Conversely, a lower cloud would be detected at a later time.

The downward-looking beam also responds to the drizzle in the cloud when geometry permits. When flight level is 2.5 km, and the cloud base is at 2.0 km, the aircraft must be closer (approximately 12 km) before the downward-looking beam intersects the cloud. This change is less dramatic than in the upward-looking beam, since the contrast between the warm lower atmosphere and the cloud bottom is less.

Beyond the leading edge (100 km) of the cloud, the brightness temperature at +2° begins to drop. This is because the far edge of the cloud is at 125 km, and the sensor can see this more transmissive space where drizzle and cloud are not present. This can be valuable, since it might enable a pilot within an icing cloud situation to search for the nearest way out.

Since the actual distance to the cloud maybe known, an equation for distance can be fit to the difference of brightness between the +2° beam and 0° beam as the MIAS radiometer approaches the cloud. With reference to FIG. 9, the actual and predicted distances are plotted on the chart (right hand scale). The agreement is quite good thereby illustrating the possibility of an algorithm to estimate distance to an icing cloud. An estimate of distances to clouds ahead enables plotting the location of the clouds on a screen, like a radar display—without emitting a signal.

However, the brightness temperature change is not perfectly linear—the rate changes around 85 km (marked with an arrow) as the beam intersects a different liquid water content. The accuracy of an estimate of distance to the cloud may be somewhat affected by the integrated water content in the cloud. There is also an inference that cloud water content can be estimated.

This strong sensor response indicates a passive microwave sensor may detect and warn a pilot of cloud liquid water many kilometers before actually encountering the cloud. An advance estimate of the cloud water temperature can also be provided, as shown in FIG. 10.

Figure 10:
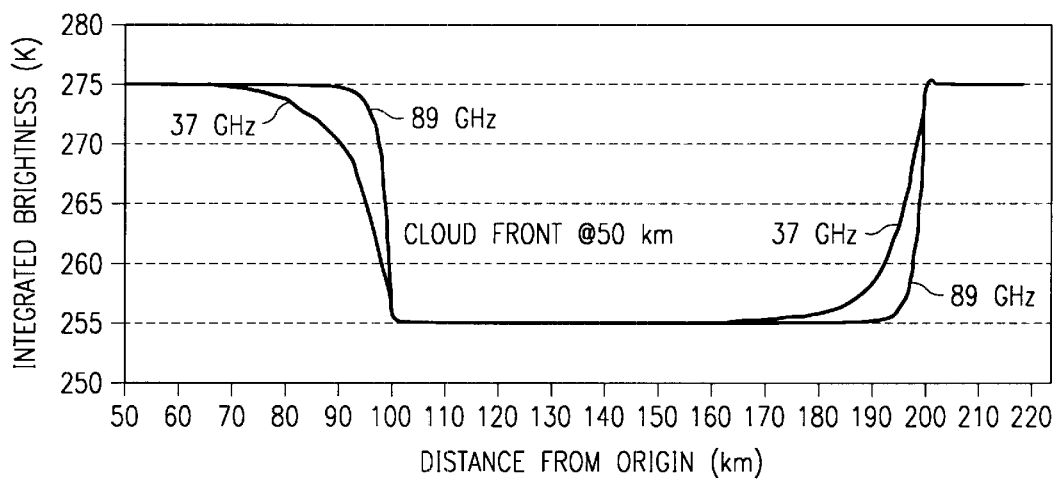
FIG. 10 is a plot of integrated brightness versus distance from origin illustrating the ability of the sensor of the MIA system of the present invention to respond to liquid water temperature changes in a cloud ahead of an aircraft.

Referring to FIG. 10, there is illustrated the brightness temperature from the 0° (horizontal) beams of the 37 GHz and 89 GHz radiometers looking ahead toward a 20° C. temperature discontinuity in a Standard Atmosphere at a flight level 2.0 km. Flight level temperature is 275.16 before the discontinuity (located at 100 km from the origin); and temperature returns to the standard value at 200 km from the origin. This is also illustrated by curves 1 and 3 of FIG. 2, thereby indicating that decreasing temperature along the path of integration leads to a lower brightness output from the sensor. In addition to demonstrating the ability to recognize temperature changes ahead of the aircraft, this also illustrates the integrated nature of the measurement. A pilot with a MIAS of the present invention could be alerted to freezing temperatures 20 km ahead, but may not show how far ahead the change to freezing temperature lies—or whether it is gradual or abrupt (as it is here). This is somewhat of a "worst case" since the temperature change is hidden within a cloud with large liquid water content (0.5 g/m^3). It should be noted that the recognition distance of a change ahead is less (about 24 km) approaching the temperature increase at 200 km. Cold cloud water is more attenuating than warm cloud water, and transmissivity between 100 and 200 km is less than in warmer air.

Another important element in warning the pilot of icing conditions ahead is an estimate of cloud water content. Because the 37 GHz and 89 GHz frequencies respond so differently to liquid water, the information of interest to a pilot will be determined from a comparison of the brightness at these two frequencies in comparable upward-looking or downward-looking beams. In Table 3 there is shown the differences between 89 GHz and 37 GHz brightness in the +2° beam for a range of liquid water content (ranging from 0.1 to 0.9 g/m^3) as the sensor of the MIAS approaches the cloud. This illustrates that estimation of water content is affected by distance. There will also be described methods to separate these two effects by comparing the two frequencies along a common path.

Figure 11:
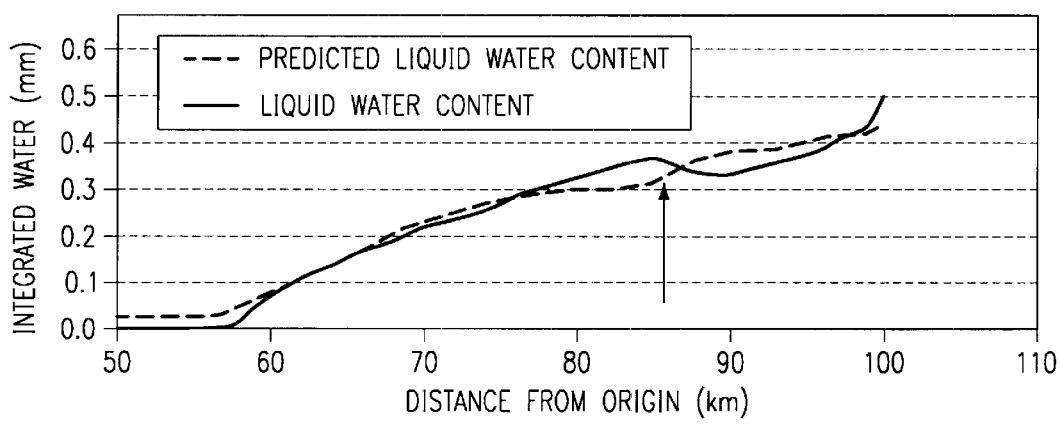
FIG. 11 is a plot of integrated water values versus distance from origin to estimate the amount of integrated liquid water viewed by the sensor of the microwave icing avoidance system of the present invention.

Referring to FIG. 11, there is shown a comparison of the actual and predicted integrated liquid water content (in mm), based on a logarithmic fit to the 37 GHz and 89 GHz brightness temperatures in the +2° beam. As in FIG. 9, there is an estimation error near 85 km, since water content is not constant.

TABLE 3

| Water Content g/m^3 | 40 km | 30 km | 20 km | 10 km | 0 km |
|---|---|---|---|---|---|
| .1 | 67 | 52 | 40 | 31 | 24 |
| .3 | 29 | 16 | 10 | 6 | 3 |
| .5 | 16 | 9 | 6 | 4 | 2 |
| .7 | 11 | 7 | 5 | 3 | 1 |
| .9 | 9 | 6 | <5 | <3 | <1 |

Because of cloud structure (only cloud in the upper kilometer, cloud plus drizzle in the lower kilometer), the upward-looking beam sees less integrated water content as the beam passes into the lower level drizzle. The drizzle was modeled according to the Marshall-Palmer size distribution, in which water content is 0.0889*R^0.84® is the rainrate, in mm/hr.). A drizzle rate of 1 mm/hr actually contains less water than the upper level cloud water content modeled as 0.1 gm/m^3. This slight pause in the brightness temperature increase was previously illustrated in FIG. 9 between 83 km and 86 km, as the beam passed from the cloud to the drizzle—that is, from more to less integrated water content.

It should be noted that the MIAS sensor does not see all the cloud water along the +2° beam. This is a consequence of the integrated nature of the sensor response. A cloud water density of 1 gram per cubic meter, integrated along a 1 km path, results in 1 mm of integrated water. Since the cloud illustrated in FIG. 6 is 25 km in length, and the water content in the upper layer is 0.1 gm/m^3, all the cloud water along the path would integrate to 2.5 mm although only a fraction of that total (0.5 mm) is detected.

Although the estimated water content is low (less than 1 mm), the icing danger is not negligible, since drizzle is present. By including scattering of the radiance from drizzle-sized drops, the effect is to introduce polarization in the received signal—that is, the vertical and horizontal components of the brightness temperature will be slightly different. Such a signal will provide clear evidence of drizzle, independent of the estimated water content. It should be noted that the noise level of the MIAS sensor is expected to be 0.2° K or less with an integration time of less than a second. Thus, time averaging over a few seconds will be sufficient to reduce sensor noise to much less than the real polarization signal. The presence of polarization—large or small—is a warning of the presence of drizzle-sized drops and the threat of clear icing.

Icing, like tornadoes and other environmental dangers, is often overforecast—that is, the forecast identifies the area and time span within which icing is possible. However, not every path through the area will result in icing. Local factors, such as the exhaust stack from a power plant, or rising motion over a range of hills, or passage through a frontal zone, may enhance deposition of ice on the aircraft.

Not all pilots need the same information. Many pilots have neither the deicing equipment on board their aircraft nor the training and experience to fly in icing conditions. The fundamental information requirement for this class of pilots is relatively simple:

1) is there liquid water ahead (not ice clouds, already frozen);
2) is the liquid water supercooled (below 273° K).

Affirmative answers to these questions require a diversion if the pilot is not cleared to fly in icing conditions. However, the pilot with a rating to fly in icing conditions can proceed, with attention to the liquid water content and the possible presence of large (drizzle-sized) droplets.

Figure 12:
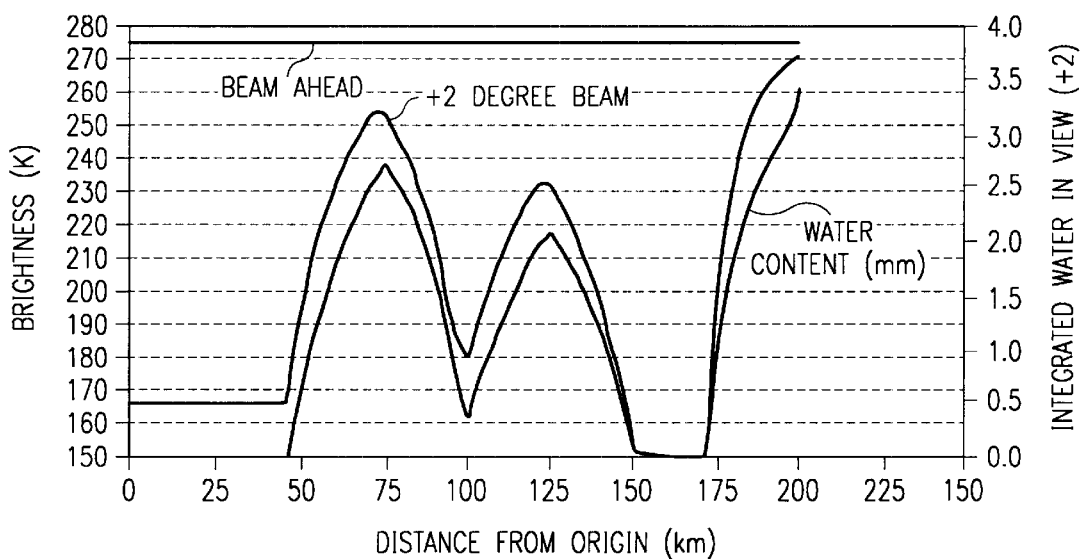
FIG. 12 is a plot of brightness versus distance from origin illustrating brightness temperature in a +2° beam that provides information to a pilot of liquid water ahead.

The most fundamental information needed by the greatest number of pilots is the presence of liquid water ahead and the temperature ahead at flight level. Referring to FIG. 12, there is plotted the output of the 37 GHz upward-looking (+2°) beam as the MIAS sensor flying at 2.0 km flight level in a Standard Atmosphere approaches a sequence of three clouds. The first cloud is located between 75 and 100 km; the second extends from 125 to 150 km; the third extends from 200 km to 300 km. The base (of all clouds) is 1.0 km and the top is 3.0 km. The first cloud contains 0.25 g/m^3 of cloud liquid water; the second cloud contains 0.15 g/m^3 of cloud liquid plus 0.15 g/m^3 of cloud-sized ice particles; the third cloud contains 0.50 g/m^3 of cloud liquid droplets. The brightness temperatures from the +2° beam and the horizontal beam are plotted against the left axis; the integrated water content (in mm) is plotted against the right axis.

A relatively simple version of the MIAS sensor, incorporating only a single frequency (37 GHz) and two beams (0° and +2°) provides the essential information for the pilot not authorized for flight into icing conditions—the presence of liquid water and the temperature ahead. As illustrated in FIG. 10, temperature changes ahead at flight level can be remotely sensed at a safe distance in the horizontal beam.

The ice in the middle cloud in FIG. 12 adds little to the brightness temperature. The already frozen droplets—which do not cause airframe icing—do not cause a "false alarm".

Brightness decreases after entering the first cloud, as the MIAS sensor "sees through" to the clearing between clouds 1 and 2. When the water content is 6.25 mm of water, there is enough penetration through the cloud (even with 6.25 mm of water) that a pilot who inadvertently entered this icing cloud could recognize clearing ahead. This is not a safe generalization, however.

Though the two beams are angled with respect to each other, the vertical distance is only 35 meters per horizontal kilometer. Ten kilometers before entering the cloud, the beams are only 350 meters apart.

The brightness temperature rise in the +2° beam is quite strong—approximately 90° K for cloud 1, and more for cloud 3 which has a more dense liquid water content (LWC).

Two measurements provide two independent pieces of information—temperature and the presence of liquid water. The temperature information is quantitative, as it needs to be, indicating the temperature to a fraction of a degree. As regards the water content information, it provides a qualitative interpretation of the brightness temperature from the upward beam, such as "low liquid water," "medium liquid water," and "high liquid water." If combined with the temperature information, a qualitative interpretation in terms of "light icing, "moderate icing," and "heavy icing" could be output.

Referring again to FIG. 12, the integrated water content seen by the MIAS sensor is plotted relative to the right hand axis (in mm). From this curve, it can be seen that when integrated water content is 0 mm, the brightness temperature is ~165 K. By the time integrated water content accumulates to 0.3 mm, the brightness temperature has risen to ~185 K. This implies that a small amount of integrated water (approximately 0.3 mm in the example) gives a good signal (about 16 K), and that a "thin" layer (100 m thick) of 0.1 g/m^3 liquid will be readily detectable. An even thinner layer (e.g., 50 m) would give a ~8 K signal, and a 25 meter thick layer would provide only a ~4 K signal—but still much larger than the expected noise level of 0.2 K.

Pilots with deicing equipment who have the experience and necessity to fly into icing conditions should still monitor environmental conditions, and especially the possible presence of drizzle-sized drops, which lead to clear icing on the airframe. An alternate embodiment of the invention will consider the measurements to be made and information to be gained from a more complex sensor. The first item of additional information is liquid water content.

Figure 13:
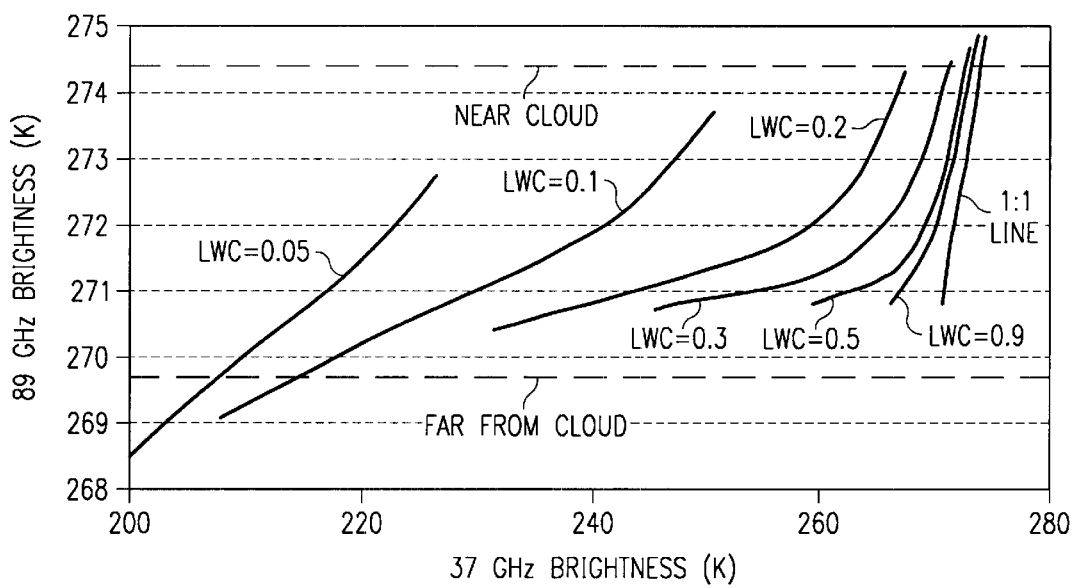
FIG. 13 is a plot of 89 GHz brightness versus 37 GHz brightness in a +2° beam as the sensor of the microwave icing avoidance system of the present invention approaches clouds of differing liquid water content.

Referring to FIG. 13, there is shown plotted the joint brightness temperatures in the +2° beam—37 GHz brightness on the horizontal axis, 89 GHz brightness on the vertical axis—as the sensor, at flight level 2.0 km, approaches a variety of clouds (base 1.0 km, top 4.0 km) of differing liquid water content, ranging from a low of 0.05 g/m^3 to a maximum of 0.9 g/m^3 liquid water content. There is an individual curve corresponding to each value of LWC. The lowest joint brightness (bottom of each curve) corresponds to maximum distance of 40 km from the cloud; the maximum joint brightness (top of each curve) corresponds to entry into the cloud. It will be noted that each curve is unique and non-overlapping. There is an asymptotic point corresponding to zero water content, which also depends on flight level. The joint brightness temperature when the sensor enters the cloud also depends on flight level.

The behavior of individual curves is in accordance with the physics of radiative transfer through clouds (Equation 1). On the left of the plot of FIG. 13, clouds with low water content cold brightness temperatures from the stratosphere and space to reach the MIAS sensor. From far away, only part of the cloud is seen, but, as the sensor approaches, more of the beam lies within the cloud (the k*ds term in Equation 1) and brightness in both frequencies increases. On the right of FIG. 13 (labeled 1:1 line) is shown the anomalous situation where brightness temperatures are identical in both frequencies. This is almost impossible with realistic cloud water content, and is suggestive of a solid object—that is, zero transmissivity (unit emissivity) in both frequencies.

Utilization of two frequencies (37GHz, 89 GHz) in the sensor offers additional information about temperature ahead at flight level. Since the 37 GHz beam has greater transmissivity (see FIG. 10), comparison of brightness temperature between the two 0° beams gives information about the rate of change of temperature ahead. In addition, if the 89 GHz beam is seeing cloud in the downward-looking direction, comparison with the 0° beam indicates whether temperature increases or decreases with decreasing altitude.

Increased information for better flight safety requires an increase of measurement variables. In response to this fundamental law of physics, a MIAS includes two angles at a single frequency, additional information from an additional frequency, and a polarization measurement, which adds further information and will now be described. Thus far, all measurements have been of atmospheric emission, which is unpolarized—that is, the energy in the vertical plane of polarization is equal to the energy in the horizontal plane of polarization. It should be noted that the horizontal beam—pointed at 0° elevation ahead of the aircraft—could be of any polarization. The word "horizontal" in this description is geometric, not electrical. Introduction of the measurement of polarization adds more information.

The reasons for expecting a polarized signal when drizzle-sized drops are present were previously discussed. The magnitude of polarization (vertical brightness—horizontal brightness) depends more on the nature of the surface below—the source of the scattered flux—than on the drizzle drops. Even when the surface flux is unpolarized, a polarization signal of a few tenths of a Kelvin from the sensor can be expected. Although this is close to the sensor's noise level, time integration of the vertical and horizontal energy from the 89 GHz beam over a few seconds would be sufficient to reveal a warning of drizzle drops.

Naturally, flight level temperature ahead must continue to be monitored, since it is supercooled drizzle that is the icing hazard. Warm drizzle does not form ice unless the aircraft surface is already below freezing as a result of flight at higher, colder altitude.

As previously discussed, frozen drizzle drops do scatter microwave radiation. Therefore frozen drizzle drops could give a "false alarm" warning of drizzle that does not cause icing.

Heretofore, there has been discussed sensor implementations, providing temperature, presence of liquid water, liquid water content, and warning of drizzle-sized drops. In FIG. 13, it was pointed out that there is a "signature"—the 1:1 line at the right hand edge of the figure—that is indicative of danger in the form of a solid obstacle ahead. The advantage of a reliable distance algorithm would provide the opportunity to scan the field of view of the MIAS sensor over some angular arc ahead of an aircraft and present a two-dimensional plot of icing conditions, for the sake of better avoidance.

As illustrated in FIG. 9, it is possible to fit a logarithmic curve to the difference between the 0° and +2° brightness temperatures which closely approximated the actual distance to the cloud. With reference to FIG. 9, it was also shown that a variation of LWC in the beam had an effect on the estimate—an error is introduced.

The height of the cloud ahead, relative to flight level, is a free variable in the atmosphere, and with only the angular difference known, it is difficult to solve for other dimensions of the triangle formed by the plane, the cloud ahead, and the top seen by the upward beam. This necessitates the use of reasonable assumptions. When only clear air (oxygen, vapor) is in the path, the sensed brightness is rather cold (as shown), since part of the path penetrates to the stratosphere and even space. When cloud liquid water enters the path, k (Equation 1) increases by an order of magnitude and the path length (s) decreases—causing the brightness to approach the brightness seen in the 0° beam as illustrated in FIG. 14.

Figure 14:
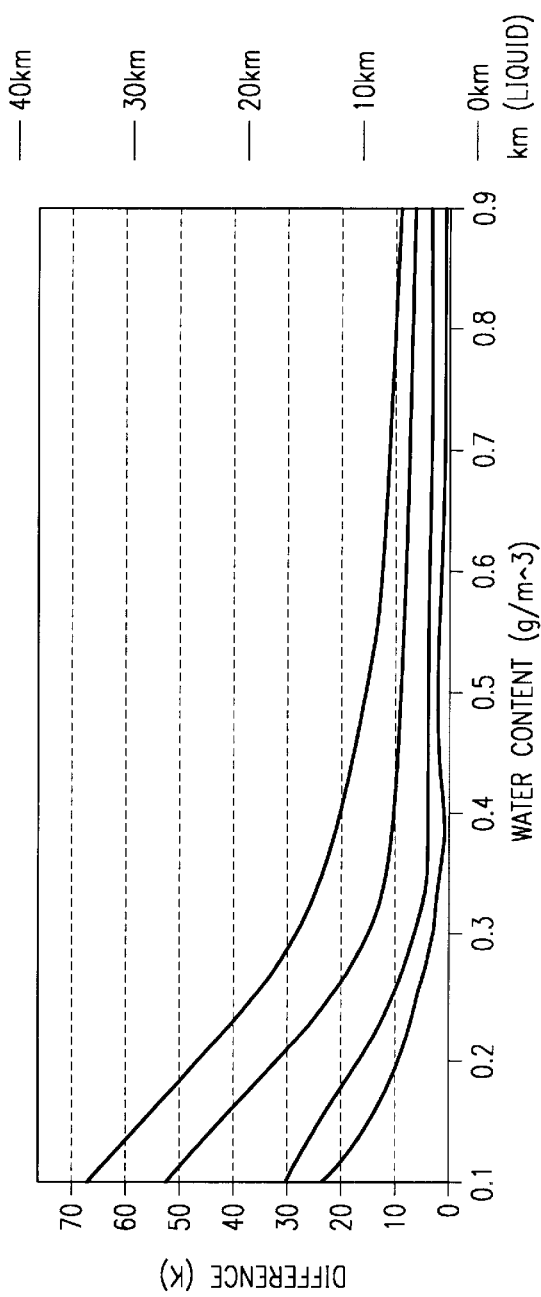
FIG. 14 is a plot of 37 GHz brightness temperature differences at various distances from clouds of varying water content.

Referring to FIG. 14, on the left side of the chart, where water content is low, more of a beam penetrates through the cloud to the stratosphere and space, depending on distance from the cloud. The top curve is for a distance of 40 km, intermediate curves are for distances of 30, 20, and 10 km, and the bottom curve is for 0 km distance. With decreasing distance (moving downward on the chart), more of the beam lies within the cloud, and the brightness temperature of the +2° beam approaches that of the 0° beam. Referring back to FIG. 1, the beam path is shown with three major parts—a low attenuation path to the cloud, a high attenuation path through the cloud, and a low attenuation path (but a very long distance) through a very cold medium—the stratosphere and space. Decreasing distance between curves illustrated in FIG. 14 corresponds to decreasing distance in FIG. 1 between the MIAS sensor and the cloud, leaving the path of integration to the cloud and the atmosphere above the cloud.

Moving to the right on the chart (increasing liquid water content), this illustrates situations where the path integration is dominated by liquid water, minimizing the contribution to a signal from the path between the sensor and cloud and the path beyond the cloud. With large liquid water content, the path above the cloud is simply not seen, and as the sensor approaches the cloud, the brightness in the upper beam approaches that in the ahead beam.

At this point, there are two potential embodiments for a "distance" algorithm. One embodiment, as discussed in connection with FIG. 13, is to use dual frequencies (37 GHz and 89 GHz), in order to independently estimate the liquid water content in the beam. The family of curves in FIG. 14 (or FIG. 13) are therefore available for use to estimate distance.

Another embodiment is to create a distance algorithm for the sensor operating at a single frequency, as discussed in connection with FIG. 10. Since the single-frequency sensor does not provide an independent estimate of liquid water content, an assumption of the LWC value must be used. The following constraints must be considered:

Preferably the error in distance estimation should be positive, i.e., underestimation of distance (actual distance is farther than the algorithm results). For safety reasons, this is better than overestimation. The pilot has more time to think or change course than estimated; and The magnitude of error should be minimized, subject to the previous constraint above.

Considering these constraints, the point on FIG. 14 where LWC=0.3 and distance to the cloud (D)=20 km, the brightness temperature difference (T)=10 K.

If a distance algorithm is based on LWC=0.3, the distance estimate will be correct (20 km). However, if the real LWC is only 0.2 (left on the chart), the estimated distance will be 0 km (a considerable underestimate). This is quite safe. The aircraft operator could probably recognize that the cloud isn't that close—especially in daylight.

If the real LWC is greater than that used in a distance algorithm (e.g. 0.4), the estimated distance is 30 km (a 10 km overestimate). This is less safe. If the real LWC is 0.5, the estimated distance is (approximately) 32 km—a little worse, but not much.

As a general principle, then, it is desired to set LWC fairly large in formulating a distance algorithm.

In examining the chart of FIG. 14, it is possible to calculate the change of apparent distance (dD) per unit change of brightness temperature difference (dT). Preferably, it is desirable to minimize this rate of change to minimize error in the distance estimate. Graphically, this means maximizing the vertical spacing between distance isopleths at several horizontal locations. It is then apparent that:

$dD/dT=0.77 @ LWC=0.3$ $dD/dT=0.71 @ LWC=0.2$ $dD/dT=0.67 @ LWC=0.1$ between 40 km and 30 km (units of km/K). Slightly smaller magnitudes may be found between 30 km and 20 km, and between 20 km and 10 km, but the trend is the same. Vertical spacing between distance isopleths is greater on the left than farther right. Minimizing the error in distance estimation therefore represents a compromise with the criterion to try to ensure underestimation of the distance rather than overestimation. The following example is based on an assumption of 0.25 g/m^3 LWC in the distance algorithm.

If LWC is set to 0.25 g/m^3 and true distance is 20 km, the difference temperature is 16 K. An algorithm based on this relationship (for flight at FL 2.0 km in a standard atmosphere) gives the following distance estimates for a 16 K temperature difference when the LWC is as shown in Table 4:

TABLE 4

| LWC (g/m^3) | Estimated Distance (km) | Comment |
| --- | --- | --- |
| 0.15 | 0 | Very safe: true distance much greater |
| 0.20 | 8 | Safe: true distance 12 km greater |
| 0.25 (truth) | 20 (truth) | Truth |
| 0.30 | 30 | Less safe: true distance only 20 km |
| 0.30 | 33 | Less safe: true distance only 20 km |

Increasing the assumed LWC in the distance algorithm increases safety—especially minimizing the danger of encountering high water content sooner than expected, as occurs in the last two rows of Table 5. It should be remembered that the distance algorithm, whether based on a dual-frequency estimate of water content or an assumed (constant) value, is valid for flight in clear air while approaching a liquid water cloud ahead. It is not valid while flying in a cloud.

What has been described are embodiments of algorithms for recognizing icing conditions ahead (temperature, liquid water presence), as well as more quantitative algorithms to measure the amount of liquid, to estimate distance (with or without assumptions about liquid water content), and warning signs that drizzle is ahead. These are summarized in Table 5.

TABLE 5

| Environment | Single Frequency Sensor | Dual Frequency Sensor | Dual Frequency Sensor, Dual Polarization @ 89 GHz |
| --- | --- | --- | --- |
| Flight Level Temperature | Monitor 0° brightness = flight level temperature. Monitor trend of 0° brightness for changes | Monitor both 0° beam temperatures. Lower frequency beam is farther ahead. | Monitor both 0° beam temperatures. Lower frequency beam is farther ahead. |
| Liquid Water ahead | Monitor + 2° beam <179K = Clear <200K = light LWC <225K = Moderate <275K = Heavy LWC | See below | See below |
| Liquid Water Content (quantitative) | Not available from single frequency | Compare low frequency and high frequency brightness; see FIG. 11. | Compare low frequency and high frequency brightness; see FIG. 13. |
| Distance | Assume LWC = 0.25 See FIG. 12 | Use quantitative LWC from FIG. 11 Use FIG. 12 for distance. | Use quantitative LWC from FIG. 13 Use FIG. 14 for distance. |
| Drizzle | Not available from single frequency | Not available from dual frequency | Monitor 89 GHz polarization (Tv - Th); any amount of polarization is a danger signal. |

Figure 15:
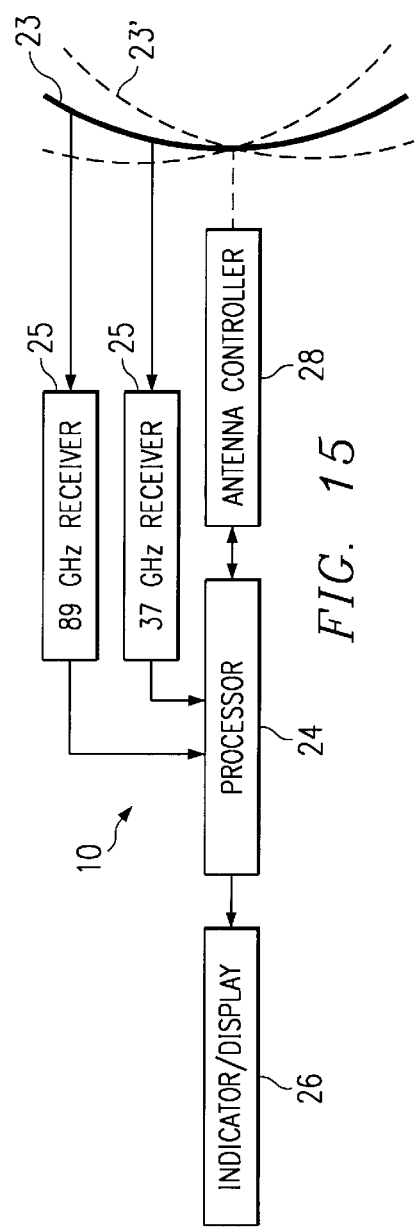
FIG. 15 is a block diagram of the microwave icing avoidance system of the present invention.

Referring to FIG. 15, there is shown details of the MIAS mounted in the aircraft 11 of FIG. 1. The MIAS 10 includes a computer or processor 24 that transmits signals to and receives signals from the other components of the MIAS 10, processes the data obtained from input signals to obtain the information and supply the indications and displays of that information noted above and described below. The processor 24 controls through an antenna controller 28 the position of the antenna 23, forming the upward-looking beams 14, 15 and the downward-looking beams 18, 19, as illustrated in FIG. 1. Receivers 25 receive microwave signals from the antenna 23 and are chosen so the hydrometeors in the icing conditions 12 have measurably different emission characteristics. The signals generated by each of the receivers 25 are applied to the processor 24.

The pilot receives an indication of icing conditions ahead of the aircraft 11 from the processor 24 through a display 26 connected to the processor.

Figure 16:
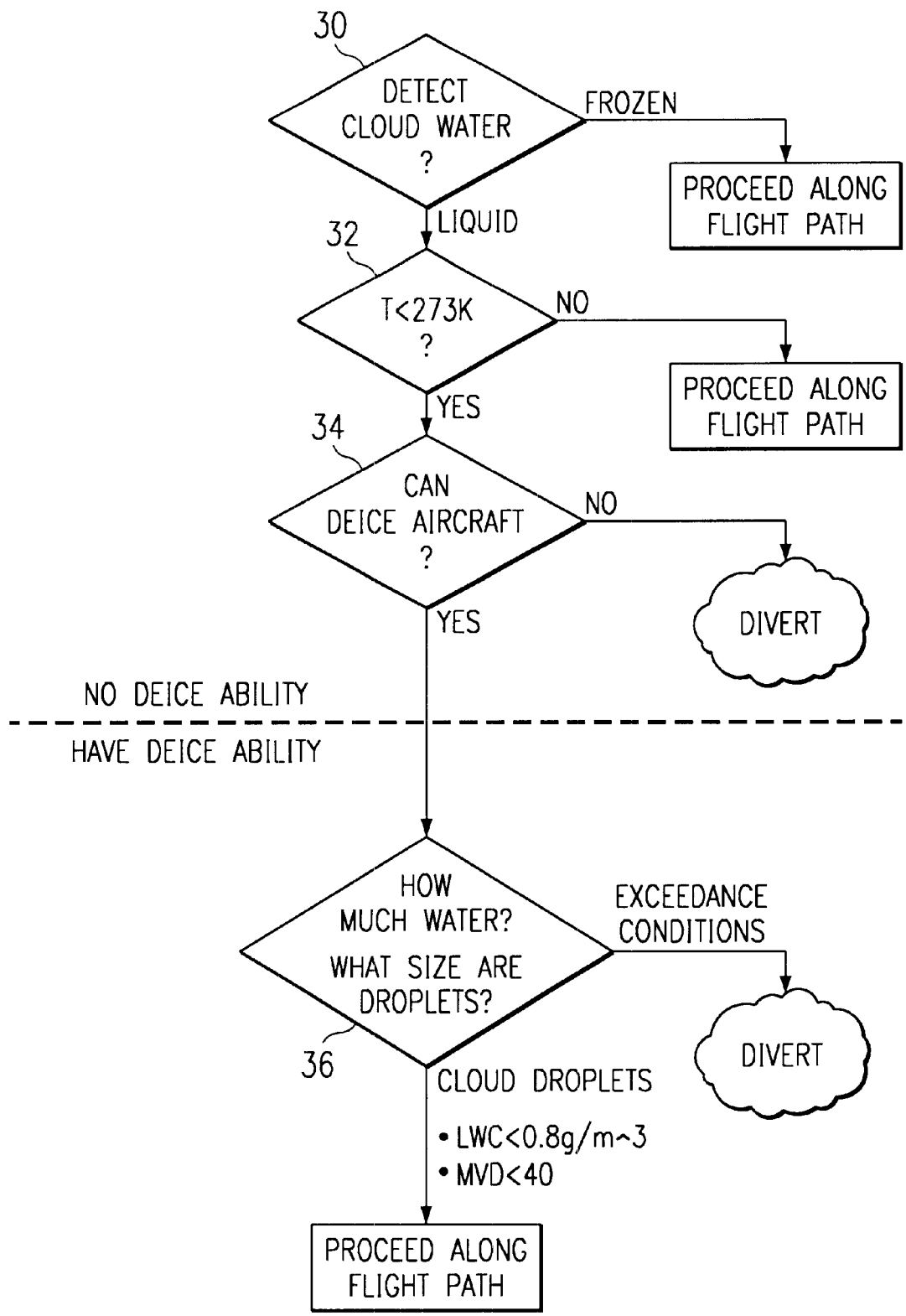
FIG. 16 is a flow chart illustrating the operation of the processor for determining icing condition in a cloud bank.

The process for generating icing condition indications is diagramed in FIG. 16. The MIAS 10 detects the presence of cloud liquid water ahead of the aircraft 11. If there is cloud liquid water ahead of the aircraft 11 then the indication presented to the pilot by the display 26 is to proceed along the flight path. If there is cloud liquid water ahead of the aircraft then the MIAS 10 determines if the temperature of the cloud liquid is above the freezing temperature. For a temperature above freezing, the indication presented to the pilot at the display 26 is to proceed along the flight path.

Referring to FIG. 16, there is illustrated logic processing computed by the processor 24 of FIG. 15. Initially, the processor 24, in response to data input from the receivers 25, performs logic processing 30 to detect cloud water 12 (see FIG. 1). If logic processing 30 detects frozen cloud water, the processor 24 generates a signal to the indicator/display 26 to instruct the pilot of the aircraft to proceed along the existing flight path. As previously explained, frozen cloud water provides little danger for icing on the aircraft. When the logic processing 30 detects liquid cloud water, then the processor 24 completes logic processing 32. When the result of logic processing 32 is that the cloud water temperature is above 273 K, then a signal is sent to the pilot of the aircraft 11 by means of the indicator/display 26 to proceed along the established flight path. However, when the logic processing 32 determines that the cloud water liquid is below 273 K, then the processor 24 advances to compute logic processing 34 to evaluate if the aircraft 11 is equipped with deicing capabilities.

When the result of logic processing 36 indicates that the conditions for icing within the cloud 12 exceeds the exceedance conditions of the aircraft's deicing capabilities, then the processor 24 generates a signal to the pilot of the aircraft 11 by means of the indicator/display 26 to divert from the present flight path. However, when logic processing 36 determines that the cloud droplets have an LWC less than 0.8 g/m^3 and the Mean Volume Diameter (MVD) is less than 40 micrometers, then the processor 24 generates a signal to the pilot of the aircraft 11 by means of the indicator/display 26 to proceed along the flight path.

What has been described is the use of passive microwave sensors, utilizing three angled beams of observation (+2°, 0°, and −2°) and two frequencies (37 GHz, 89 GHz). Passive microwave sensors are well-suited to recognition of the conditions leading to aircraft icing. The system described and claimed is passive and is suitable for covert operations in battlefield conditions.

It is reasonable to provide a simpler sensor at lower cost, using only the 37 GHz frequency, for pilots who are not equipped to fly into icing clouds. This sensor provides information about temperature and the presence of liquid water ahead necessary to avoid icing. It also provides ability to see out and/or through an icing cloud in case of inadvertent entry.

The addition of 89 GHz sensor provides more quantitative icing information (liquid water content, warning of drizzle) for pilots equipped to fly in icing conditions to monitor the degree and type of icing to be expected.

Although several embodiments of the invention have been illustrated in the accompanying drawings and described in the foregoing detailed description, it will be understood that the invention is not limited to the embodiments disclosed, but is capable of numerous modifications without departing from the scope of the invention as claimed.

What is claimed is:

1. A passive microwave icing avoidance system for aircraft guidance, comprising:
    a first receiver responsive to received air temperature and cloud hydrometeors at a first microwave frequency having emission characteristics from along an upward beam path, a downward beam path and a forward beam path, each beam path having an angle with reference to the flight path of an aircraft, the hydrometeors likely to cause icing conditions, said first receiver having output data related to the air temperature and cloud hydrometeors for each of the beam paths;
    a second receiver responsive to received air temperature and cloud hydrometeors at a second microwave frequency having measurable different emission characteristics from the first microwave frequency from along an upward beam path, a downward beam path and a forward beam path, each beam path having an angle with reference to the flight path of the aircraft, the hydrometeors likely to cause icing conditions, said second receiver having output data related to the air temperature and cloud hydrometeors for each of the beam paths;
    a processor receiving the output data from the first and second receivers, said processor operational to compare output data for each beam path and compute potential icing conditions and generating aircraft guidance signals indicating icing or no icing conditions; and
    an indicator/display responsive to the guidance signals to present audio/visual aircraft guidance related to actual or potential icing conditions.

2. The passive microwave icing avoidance system as set forth in claim 1, further comprising:
    an antenna responsive to position controls from said processor to receive cloud hydrometeors from along the beam paths and transmitting sensed microwave energy to the first and second receivers.

3. The passive microwave icing avoidance system as set forth in claim 1, wherein said first receiver comprises:
    a receiver responsive to passive remote sensing microwave energy at about 37 GHz; and
wherein said second receiver comprises:
    a receiver responsive to passive remote sensing microwave energy at about 89 GHz.

4. The passive microwave icing avoidance system as set forth in claim 3, wherein said second receiver comprises:
    a receiver responsive to vertical and horizontal polarized microwave energy.

5. A passive microwave icing avoidance system for aircraft guidance, comprising:
    a receiver responsive to receive air temperature and cloud hydrometeors at passive remote sensing microwave energy from along an upward beam path and a forward beam path, each beam path having an angle with reference to the flight path of an aircraft, the hydrometeors likely to cause icing conditions, said receiver having output data related to the air temperature and cloud hydrometeors;
    a processor receiving the output data from the receiver, said processor operational to compare output data for each beam path and compute potential icing conditions and generating aircraft guidance signals indicating temperature of the cloud hydrometeors and actual icing or potential icing conditions; and
    an indicator/display responsive to the guidance signals to present audio/visual aircraft guidance related to actual or potential icing conditions.

6. The passive microwave icing avoidance system as set forth in claim 5 further comprising:
    an antenna responsive to position controls from said processor to receive microwave frequency energy related to cloud hydrometeors from along the beam paths and transmitting the received microwave energy to the receiver.

7. The passive microwave icing avoidance system as set forth in claim 6 wherein said receiver comprises:
    a receiver responsive to passive remote sensing microwave energy in the range from about 36 GHz to about 37 GHz.

8. A method for passive monitoring of cloud hydrometeors for potential aircraft icing conditions, comprising:

detecting passive remote sensing microwave signal energy from along at least an upward beam path and a forward beam path, each beam path having an angle with reference to the flight path of an aircraft;

comparing the passive remote sensing microwave signal energy from along at least the upward beam path and the forward beam path to generate a determination of a frozen water or a supercooled water condition of cloud water; and in response to a determination of frozen water, generating a message to an aircraft operator to proceed along a flight path into the cloud water.

9. The method for passive monitoring of cloud hydrometeors as set forth in claim 8 further comprising:

in response to a determination of supercooled water, determining the temperature of the supercooled water.

10. The method for passive monitoring of cloud hydrometeors as set forth in claim 9 further comprising:

in response to a determination of supercooled water and the temperature of the supercooled water, generating a message to an aircraft operator to divert from a flight path to avoid the supercooled water.

11. The method for passive monitoring of cloud hydrometeors as set forth in claim 8 wherein detecting passive remote sensing microwave signal energy comprises:

measuring microwave energy radiation emitted from the cloud water and surrounding atmosphere.

12. The method for passive monitoring of cloud hydrometeors as set forth in claim 11 wherein detecting microwave signal energy further comprises:

measuring passive remote sensing microwave energy radiation emitted from cloud water in the range of from about 36 GHz to about 37 GHz.

13. The method for passive monitoring of cloud hydrometeors as set forth in claim 11 wherein detecting microwave signal energy further comprises:

measuring passive remote sensing microwave energy radiation emitted from cloud water in the range of from about 36 GHz to about 37 GHz and also in the range of from about 86 GHz to about 92 GHz.

14. A method for passive monitoring of cloud hydrometeors for potential aircraft icing conditions, comprising:

detecting passive remote sensing microwave signal energy along an upward beam path, a downward beam path and a forward beam path, each beam path having an angle with reference to the flight path of an aircraft;

comparing the detected microwave signal energy along the upward beam path, the downward beam path and the forward beam path to generate a determination of atmospheric temperature and frozen water or supercooled water for cloud water;

determining the size of water droplets in the cloud water in response to a determination of supercooled water and the availability of icing equipment on the aircraft; and in response to a determination that the conditions for icing on an aircraft exceeds the capabilities of the deicing equipment, generating a message to an aircraft operator to divert from the present flight path.

15. The method for passive monitoring of cloud hydrometeors as set forth in claim 14 wherein detecting passive remote sensing microwave signal energy comprises:

measuring passive remote sensing microwave energy radiation emitted from the cloud water in the range of from about 36 GHz to about 37 GHz along one beam path extending along the flight level of the aircraft, one beam path extending at a positive angle with reference to the flight level of the aircraft, and one beam path extending at a negative angle with reference to the flight level of the aircraft; and measuring passive remote sensing microwave energy radiation emitted in the range from about 86 GHz to about 92 GHz from one beam path extending along the flight level of the aircraft, one beam path extending at a positive angle with reference to the flight level of the aircraft, and one beam path extending at a negative angle with reference to the flight level of the aircraft.

16. The method for passive monitoring of cloud hydrometeors as set forth in claim 15 wherein measuring the passive remote sensing microwave energy radiation emitted in the range of from about 86 GHz to about 92 GHz comprises measuring vertical polarization and horizontal polarization.

17. The method for passive monitoring of cloud hydrometeors as set forth in claim 14 further comprising:

in response to detecting passive remote sensing microwave signal energy, determining the temperature of the cloud water as above or below a threshold temperature and the capability of freezing on aircraft surfaces.

18. The method for passive monitoring of cloud hydrometeors as set forth in claim 17 wherein determining the temperature of the cloud water comprises:

determining when the cloud water comprises supercooled droplets.

19. The method for passive monitoring of cloud hydrometeors as set forth in claim 18 further comprising:

in response to a determination of cloud water temperature above the threshold temperature, generating a message to an aircraft operator to proceed along the flight path into the cloud water.

20. The method for passive monitoring of cloud hydrometeors as set forth in claim 14 further comprising determining the amount of supercooled water to form ice on aircraft surfaces that exceeds the capability of deicing equipment.

21. The method for passive monitoring of cloud hydrometeors as set forth in claim 20 further comprising:

in response to a determination that the conditions for icing of aircraft surfaces, generating a message to an aircraft operator to divert from the present flight path.

22. The method for passive monitoring of cloud hydrometeors as set forth in claim 8 further comprising:

determining the size of water droplets in the cloud water; and in response to a determination that the size of droplets in the cloud water exceeds a given threshold, generating a message to an aircraft operator to divert from the present flight path.

23. The method for passive monitoring of cloud hydrometeors as set forth in claim 14 further comprising:

in response to a determination of frozen water, generating a message to an aircraft operator to proceed along a flight path into the cloud water.

24. A passive all-weather imaging system, comprising:

an antenna responsive to position controls to receive microwave energy emissions from along an upward beam path, a downward beam path and a forward beam path and outputting signals representing the received microwave energy emissions;

a first receiver responsive to signals received from the antenna representing a first microwave frequency having emission characteristics from along the upward beam path, the downward beam path and the forward beam path, the downward beam path and the upward beam path having an angle with reference to the forward beam path, the first receiver having output data related to the microwave energy emissions of each of the beamed paths;

a second receiver responsive to signals from the antenna representing a second microwave frequency having measurable different emission characteristics from the first microwave frequency from along the upward beam path, the downward beam path and the forward beam path, the upward beam path and the downward beam path having an angle with reference to the forward beam path, the second receiver having output data related to the microwave energy emissions for each of the beam paths;

a processor receiving the output data from the first and second receivers, the processor operational to compare output data for each beam path and generating signals representing weather conditions; and a display responsive to the weather signals to present audio/visual imagery relating to observed weather conditions.

25. The all-weather imaging system as set forth in claim 24 wherein the first receiver comprises:

a receiver responsive to passive remote sensing microwave energy at about 37 GHz; and wherein the second receiver comprises:

a receiver responsive to passive remote sensing microwave energy at about 89 GHz.

26. The passive all-weather imaging system as set forth in claim 24 wherein the second receiver comprises:

a receiver responsive to vertical and horizontal polarized microwave energy.

27. The all-weather imaging system as set forth in claim 24 wherein the first and second microwave frequencies comprise frequencies limited to remote sensing.

28. A method for passive monitoring of microwave energy emissions for all weather imaging, comprising:

detecting passive remote sensing microwave energy emissions from along at least an upward beam path and a forward beam path, each beam path having an angle with reference to the forward beam path;

comparing the passive remote sensing microwave energy from along at least the upward beam path and the forward beam path to generate a determination of weather conditions; and in response to a determination of weather conditions, generating a message to a display to image the weather conditions.

29. The method for passive monitoring of microwave energy emissions as set forth in claim 28 wherein detecting passive remote sensing microwave energy comprises:

measuring microwave energy radiation emitted from water, ice and surrounding atmosphere.

30. The method for passive monitoring of microwave energy emissions as set forth in claim 28 wherein detecting passive remote sensing microwave energy further comprises:

measuring passive remote sensing microwave emitted radiation in the range of from 36 GHz to about 37 GHz.

31. The method for passive monitoring of microwave energy emissions as set forth in claim 28 wherein detecting microwave signal energy further comprises:

measuring passive remote sensing microwave energy radiation emitted in the range of from about 36 GHz to about 37 GHz and also in the range of from about 86 GHz to about 92 GHz.

32. A passive microwave icing avoidance system for aircraft guidance, comprising:

a first receiver responsive to receive air temperature and cloud hydrometeors at passive remote sensing microwave energy at about 37 GHz from along a plurality of beam paths, each beam path having an angle with reference to the flight path of an aircraft, the hydrometeors likely to cause icing conditions, the first receiver having output data related to the air temperature and cloud hydrometeors for each of the plurality of beam paths;

a second receiver responsive to receive air temperature and cloud hydrometeors at passive remote sensing microwave energy at about 89 GHz from along a plurality of beam paths, each beam path having an angle with reference to the flight path of the aircraft, the hydrometeors likely to cause icing conditions, the second receiver having output data related to the air temperature and cloud hydrometeors for each of the plurality of beam paths;

a processor receiving the output data from the first and second receivers, the processor operational to process the output data of the receivers and compute potential icing conditions and generating aircraft guidance signals indicating icing or no icing conditions; and an indicator/display responsive to the guidance signals to present audio/visual aircraft guidance related to actual or potential icing conditions.

33. The passive microwave icing avoidance system as set forth in claim 32 wherein the second receiver comprises:

a receiver responsive to vertical and horizontal polarized microwave energy.

34. A method for passive monitoring of cloud hydrometeors for potential aircraft icing conditions, comprising:

measuring passive remote sensing microwave energy radiation emitted in the range of from about 36 GHz to about 37 GHz and also in the range of from 86 GHz to about 92 GHz from along a plurality of beam paths, each beam path having an angle with reference to the flight path of an aircraft;

generating from the microwave emitted radiation a determination of frozen water or a super cooled water condition of cloud water; and in response to a determination of frozen water, generating a message to an aircraft operator to proceed along a flight path into the cloud water.

35. A method for passive monitoring of cloud hydrometeors for potential aircraft icing conditions, comprising:

measuring passive remote sensing microwave energy radiation emitted from cloud water in the range of from 36 GHz to about 37 GHz from along a plurality of beam paths, each beam path having an angle with reference to the flight path of an aircraft;

generating from the microwave emitted radiation a determination of frozen water or a super cooled water condition of cloud water; and in response to a determination of frozen water, generating a message to an aircraft operator to proceed along a flight path into the cloud water.

36. A method for passive monitoring of cloud hydrometeors for potential aircraft icing conditions, comprising:

measuring passive remote sensing microwave energy radiation emitted from the cloud water in the range of from about 36 GHz to about 37 GHz along one beam path extending along the flight level of the aircraft, one beam path extending at a positive angle with reference to the flight level of the aircraft, and one beam path extending at a negative angle with reference to the flight level of the aircraft;

measuring passive remote sensing microwave energy radiation emitted in the range of from about 86 GHz to about 92 GHz from one beam path extending along the flight level of the aircraft, one beam path extending at a positive angle with reference to the flight level of the aircraft, and one beam path extending at a negative angle with reference to the flight level of the aircraft;

generating from the measured microwave emitted radiation along the beam paths a determination of atmospheric temperature and frozen water or super cooled water for cloud water;

determining the size of water droplets in the cloud water in response to a determination of super cooled water and the availability of icing equipment on the aircraft;

in response to a determination that the conditions for icing of an aircraft exceed the capabilities of the deicing equipment, generating a message to an aircraft operator to divert from the present flight path.

37. The method for passive monitoring of cloud hydrometeors as set forth in claim 36 wherein measuring the passive remote sensing microwave energy radiation emitted in the range of from about 86 GHz to about 92 GHz comprises measuring a vertical polarization and horizontal polarization.

\* \* \* \* \*

UNITED STATES PATENT AND TRADEMARK OFFICE
CERTIFICATE OF CORRECTION

PATENT NO. : 6,489,915 B1
DATED : December 3, 2002
INVENTOR(S) : R. Todd Lines et al.

It is certified that error appears in the above-identified patent and that said Letters Patent is hereby corrected as shown below:

Column 2,
Line 43, after "path.", delete "to".

Column 4,
Line 21, after "plot", delete "ofbrighness", and insert -- of brightness --.

Column 7,
Line 29, after "lower", delete "25".
Line 53, after "manifestation", delete "ofKirchoff s", and insert -- of Kirchoff's --.

Column 9,
Line 34, after "frequencies (", delete 37Ghz, and insert -- 37 GHz --.

Column 10,
Line 45, after "in the", delete "—".

Column 11,
Line 67, after "(bottom curve)", delete "f or", and insert -- for --.

Signed and Sealed this

Twenty-second Day of April, 2003

JAMES E. ROGAN
*Director of the United States Patent and Trademark Office*